(12) United States Patent
Saha et al.

(10) Patent No.: US 9,750,942 B2
(45) Date of Patent: Sep. 5, 2017

(54) SYSTEMS AND METHODS FOR DETERMINING PARAMETERS FOR EACH OF A PLURALITY OF VECTORS

(71) Applicant: Cardiac Pacemakers, Inc., St. Paul, MN (US)

(72) Inventors: Sunipa Saha, Shoreview, MN (US); Keith L. Herrmann, Minneapolis, MN (US); Yinghong Yu, Shoreview, MN (US); David W. Yost, Brooklyn Park, MN (US); Holly E. Rockweiler, Palo Alto, CA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 139 days.

(21) Appl. No.: 14/575,099

(22) Filed: Dec. 18, 2014

(65) Prior Publication Data

US 2015/0165212 A1  Jun. 18, 2015

Related U.S. Application Data

(60) Provisional application No. 61/917,842, filed on Dec. 18, 2013.

(51) Int. Cl.
*A61N 1/37* (2006.01)
*A61N 1/368* (2006.01)
*A61N 1/36* (2006.01)

(52) U.S. Cl.
CPC ............ *A61N 1/371* (2013.01); *A61N 1/3686* (2013.01); *A61N 1/36114* (2013.01); *A61N 1/37* (2013.01)

(58) Field of Classification Search
CPC ......... A61N 1/371; A61N 1/3686; A61N 1/37
USPC ...................................................... 607/17, 28
See application file for complete search history.

(56) References Cited

U.S. PATENT DOCUMENTS

| | | | |
|---|---|---|---|
| 6,128,535 | A | 10/2000 | Maarse |
| 6,192,275 | B1 | 2/2001 | Zhu et al. |
| 6,226,551 | B1 | 5/2001 | Zhu et al. |
| 6,421,564 | B1 | 7/2002 | Yerich et al. |
| 6,463,327 | B1 | 10/2002 | Lurie et al. |
| 6,493,586 | B1 | 12/2002 | Stahmann et al. |
| 6,587,726 | B2 | 7/2003 | Lurie et al. |
| 6,615,089 | B1 | 9/2003 | Russie et al. |
| 6,772,008 | B2 | 8/2004 | Zhu et al. |
| 6,922,589 | B2 | 7/2005 | Stahmann et al. |

(Continued)

OTHER PUBLICATIONS

Rogers, D. P., P. D. Lambiase, M. D. Lowe and A. W. Chow. A randomized double-blind crossover trial of triventricular versus biventricular pacing in heart failure. Eur J Heart Fail 2012;14(5): 495-505.

(Continued)

*Primary Examiner* — Carl H Layno
*Assistant Examiner* — Jon Eric C Morales
(74) *Attorney, Agent, or Firm* — Schwegman Lundberg & Woessner, P.A.

(57) ABSTRACT

Systems and methods for efficiently determining one or more parameters for vectors of a multi-electrode implantable medical device, and for identifying one or more suitable vectors for sensing cardiac electrical data and/or delivering electrical stimulation therapy based on one or more of the determined parameters. Reducing the time required to determine the one or more parameters for each vector can help reduce procedure time for implanting and/or configuring an implantable medical device, which can reduce costs and/or improved patient comfort.

20 Claims, 8 Drawing Sheets

(56) References Cited

U.S. PATENT DOCUMENTS

| | | |
|---|---|---|
| 6,937,901 B2 | 8/2005 | Zhu et al. |
| 6,978,178 B2 | 12/2005 | Sommer et al. |
| 7,031,773 B1 | 4/2006 | Levine et al. |
| 7,123,963 B2 | 10/2006 | Sawchuk et al. |
| 7,200,439 B2 | 4/2007 | Zdeblick et al. |
| 7,225,016 B1 | 5/2007 | Koh |
| 7,225,035 B2 | 5/2007 | Brabec et al. |
| 7,228,174 B2 | 6/2007 | Burnes et al. |
| 7,277,757 B2 | 10/2007 | Casavant et al. |
| 7,299,093 B2 | 11/2007 | Zhu et al. |
| 7,328,067 B2 | 2/2008 | Zhu et al. |
| 7,340,302 B1 | 3/2008 | Falkenberg et al. |
| 7,363,086 B1 | 4/2008 | Koh et al. |
| 7,392,086 B2 | 6/2008 | Sathaye |
| 7,412,287 B2 | 8/2008 | Yonce et al. |
| 7,469,161 B1 | 12/2008 | Gandhi et al. |
| 7,471,983 B2 | 12/2008 | Voegele et al. |
| 7,496,409 B2 | 2/2009 | Greenhut et al. |
| 7,509,170 B2 | 3/2009 | Zhang et al. |
| 7,555,336 B2 | 6/2009 | Sheth et al. |
| 7,555,340 B2 | 6/2009 | Dong et al. |
| 7,587,240 B2 | 9/2009 | Zhang et al. |
| 7,620,452 B1 | 11/2009 | Russie |
| 7,657,314 B2 | 2/2010 | Sathaye et al. |
| 7,680,536 B2 | 3/2010 | Sathaye et al. |
| 7,711,423 B2 | 5/2010 | Burnes et al. |
| 7,734,333 B2 | 6/2010 | Ghanem et al. |
| 7,738,959 B2 | 6/2010 | Manrodt et al. |
| 7,761,164 B2 | 7/2010 | Verhoef et al. |
| 7,792,585 B1 | 9/2010 | Shelchuk |
| 7,848,812 B2 | 12/2010 | Crowley et al. |
| 7,953,489 B2 | 5/2011 | Warren et al. |
| 7,957,803 B2 | 6/2011 | Zhang et al. |
| 7,996,072 B2 | 8/2011 | Haefner |
| 8,010,203 B2 | 8/2011 | DeMulling et al. |
| 8,014,860 B2 | 9/2011 | Kwok et al. |
| 8,036,743 B2 | 10/2011 | Savage et al. |
| 8,065,002 B2 | 11/2011 | Arand et al. |
| 8,078,276 B2 | 12/2011 | Dong et al. |
| 8,135,463 B2 | 3/2012 | Burnes et al. |
| 8,145,311 B2 | 3/2012 | Min |
| 8,150,512 B2 | 4/2012 | Bornzin et al. |
| 8,160,700 B1 | 4/2012 | Ryu et al. |
| 8,175,703 B2 | 5/2012 | Dong et al. |
| 8,185,202 B2 | 5/2012 | Sathaye |
| 8,200,331 B2 | 6/2012 | Libbus et al. |
| 8,200,332 B2 | 6/2012 | Libbus et al. |
| 8,209,010 B2 | 6/2012 | Ryu et al. |
| 8,209,013 B2 | 6/2012 | Brooke et al. |
| 8,233,979 B1 | 7/2012 | Shelchuk |
| 8,255,048 B2 | 8/2012 | Dal Molin et al. |
| 8,260,421 B2 | 9/2012 | Sathaye |
| 8,265,736 B2 | 9/2012 | Sathaye et al. |
| 8,265,755 B2 | 9/2012 | Min |
| 8,265,759 B2 | 9/2012 | Tehrani et al. |
| 8,271,086 B2 | 9/2012 | Voegele et al. |
| 8,271,087 B2 | 9/2012 | Sathaye et al. |
| 8,285,377 B2 | 10/2012 | Rosenberg et al. |
| 8,301,246 B2 | 10/2012 | Park et al. |
| 8,306,622 B2 | 11/2012 | Arcot-Krishnamurthy et al. |
| 8,326,418 B2 | 12/2012 | Sommer et al. |
| 8,326,419 B2 | 12/2012 | Rosenberg et al. |
| 8,335,565 B2 | 12/2012 | Freeberg et al. |
| 8,346,372 B2 | 1/2013 | Yang et al. |
| 8,401,646 B2 | 3/2013 | Stadler et al. |
| 8,447,400 B2 | 5/2013 | More et al. |
| 8,744,572 B1 | 6/2014 | Greenhut et al. |
| 2006/0155202 A1 | 7/2006 | Arand et al. |
| 2007/0129764 A1 | 6/2007 | Burnes |
| 2008/0077186 A1 | 3/2008 | Thompson et al. |
| 2009/0043351 A1 | 2/2009 | Sathaye et al. |
| 2009/0043352 A1 | 2/2009 | Brooke et al. |
| 2009/0054946 A1 | 2/2009 | Sommer et al. |
| 2009/0210024 A1 | 8/2009 | Brooke |
| 2010/0125306 A1 | 5/2010 | McCabe et al. |
| 2010/0152801 A1 | 6/2010 | Koh et al. |
| 2010/0198292 A1 | 8/2010 | Honeck et al. |
| 2010/0305637 A1 | 12/2010 | McCabe et al. |
| 2010/0305638 A1 | 12/2010 | McCabe et al. |
| 2010/0305647 A1 | 12/2010 | McCabe et al. |
| 2010/0324617 A1 | 12/2010 | Ong |
| 2011/0004264 A1 | 1/2011 | Siejko et al. |
| 2011/0022110 A1 | 1/2011 | Min |
| 2011/0022112 A1 | 1/2011 | Min |
| 2011/0098770 A1 | 4/2011 | Ryu et al. |
| 2011/0098773 A1 | 4/2011 | Brisben et al. |
| 2011/0098774 A1 | 4/2011 | Brisben et al. |
| 2011/0106213 A1 | 5/2011 | Davis et al. |
| 2011/0152956 A1 | 6/2011 | Hincapie Ordonez et al. |
| 2011/0196441 A1 | 8/2011 | Ryu et al. |
| 2011/0196442 A1 | 8/2011 | Ryu et al. |
| 2011/0245890 A1 | 10/2011 | Brisben et al. |
| 2011/0319954 A1 | 12/2011 | Niazi et al. |
| 2012/0035685 A1 | 2/2012 | Saha et al. |
| 2012/0078320 A1 | 3/2012 | Schotzko et al. |
| 2012/0101543 A1 | 4/2012 | Demmer et al. |
| 2012/0101546 A1 | 4/2012 | Stadler et al. |
| 2012/0130442 A1 | 5/2012 | Rockweiler et al. |
| 2012/0150253 A1 | 6/2012 | Burnes et al. |
| 2012/0185012 A1 | 7/2012 | Ryu et al. |
| 2012/0185013 A1 | 7/2012 | Sivard et al. |
| 2012/0191154 A1 | 7/2012 | Ryu et al. |
| 2012/0229496 A1 | 9/2012 | Bloemer |
| 2012/0253359 A1 | 10/2012 | Koh et al. |
| 2012/0271371 A1 | 10/2012 | Keel et al. |
| 2012/0290036 A1 | 11/2012 | Karamanoglu et al. |
| 2012/0296387 A1 | 11/2012 | Zhang et al. |
| 2012/0296388 A1 | 11/2012 | Zhang et al. |
| 2012/0323291 A1 | 12/2012 | Sathaye et al. |
| 2012/0330372 A1 | 12/2012 | Sathaye et al. |
| 2013/0006332 A1 | 1/2013 | Sommer et al. |
| 2013/0030487 A1 | 1/2013 | Keel et al. |
| 2013/0035737 A1 | 2/2013 | Ryu et al. |
| 2013/0035738 A1 | 2/2013 | Karst et al. |
| 2013/0046356 A1 | 2/2013 | Jensen et al. |
| 2013/0046369 A1 | 2/2013 | Eggen et al. |
| 2013/0053916 A1 | 2/2013 | Sambelashvili et al. |
| 2013/0053918 A1 | 2/2013 | Sambelashvili et al. |
| 2013/0183182 A1 | 7/2013 | White, Jr. |
| 2013/0261687 A1 | 10/2013 | Xi et al. |

OTHER PUBLICATIONS

Ginks, M. R., S. G. Duckett, S. Kapetanakis, J. Bostock, S. Hamid, A. Shetty, Y. Ma, K. S. Rhode, G. S. Carr-White, R. S. Razavi and C. A. Rinaldi. Multi-site left ventricular pacing as a potential treatment for patients with postero-lateral scar: insights from cardiac magnetic resonance imaging and invasive haemodynamic assessment. Europace 2012;14 (3): 373-379.

Niazi, I., J. Kiemen, P. Yong, M. Newman, J. Ding, M. Stucky, S. Arcot-Krishnamurthy and N. Yu. Hemodynamic superiority of dual-site left ventricular stimulation over conventional biventricular stimulation in heart failure patients. Journal of Innovations in Cardiac Rhythm Management 2011;2(8):412-418.

Leclercq, C., F. Gadler, W. Kranig, S. Ellery, D. Gras, A. Lazarus, J. Clementy, E. Boulogne and J. C. Daubed. A randomized comparison of triple-site versus dual-site ventricular stimulation in patients with congestive heart failure. J Am Coll Cardiol 2008;51(15): 1455-1462.

Pappone, C., S. Rosanio, G. Oreto, M. Tocchi, S. Gulletta, A. Salvati, C. Dicandia, V. Santinelli, P. Mazzone, F. Veglia, J. Ding, L. Sallusti, J. Spinelli and G. Viced Vicedomini. Cardiac pacing in heart failure patients with left bundle branch block: impact of pacing site for optimizing left ventricular resynchronization. 2000;Ital Heart J 1(7): 464-469.

Medtronic, VIVA™/VIVA™ Quad, BRAVA™/ BRAVA™ Quad CRT-D. Family of digital implantable cardioverter defibrillators with cardiac resynchronization therapy. Reference Manual, 2012. 418 Pgs.

St. Jude Medical 2013 Investor Conference. Power Point Slideshow. Feb. 1, 2013.

(56) References Cited

OTHER PUBLICATIONS

Mike Coyle, Medtronic. Executive Vice President & Cardiac and Vascular group President Medtronic Inc. Medtronic 2012 Investor Conference. Power Point Slideshow. Jun. 1, 2012. New York City.
Business Wire, Press Release. "St. Jude Medical, Inc. announced first enrollment of its MultiPoint" St. Paul, Minnesota. May 2, 2013.

| Sample Output | | | | | |
|---|---|---|---|---|---|
| Vector | PS Present | Ω | LV Capture | RV-LV Timing | R-wave Amp |
| Vector A | Yes | 750 Ω | >2.0V | 65ms | 6.2mV |
| Vector B | No | 648 Ω | <2.0V | 85ms | 14.3mV |

FIG. 5

SYSTEMS AND METHODS FOR DETERMINING PARAMETERS FOR EACH OF A PLURALITY OF VECTORS

CROSS-REFERENCE TO RELATED APPLICATIONS

This application claims priority under 35 U.S.C. §119 to U.S. Provisional Application Ser. No. 61/917,842, filed Dec. 18, 2013, the entirety of which is incorporated herein by reference.

TECHNICAL FIELD

The present disclosure generally relates to systems and methods for selecting vectors for use in a cardiac rhythm management system, and more specifically for determining parameters for each of a plurality of vectors to aid in selecting vectors.

BACKGROUND

Cardiac rhythm management devices can include implantable or ambulatory devices, such as pacemakers, cardioverter defibrillators, or devices that can monitor one or more physiological parameters, and/or provide one or a combination of pacing, defibrillation, and cardiac resynchronization therapies. Such devices can be configured for use with a plurality of implanted or external electrodes, such as to detect and/or treat cardiac conditions. These electrodes may be configured in a plurality of different combinations for sensing cardiac electrical activity or delivering electrical stimulation therapy. Using different combinations of electrodes for sensing cardiac electrical activity may produce different sensed signals. Using different combinations of electrodes for delivering electrical stimulation therapy may also result in different effectiveness of the therapy. Each of the available electrode combinations may be termed a "vector".

In some instances, several different parameters are determined for each "vector", and these parameters are used to determine the suitability of each vector for sensing and/or delivering electrical stimulation therapy. Selecting a proper vector for sensing cardiac electrical activity and/or for delivering electrical stimulation therapy can help provide more effective treatment to a patient. In some instances, the number of available vectors can be large due to the number of available electrodes. As a result, it can be time consuming to determine the various parameters for each of the available "vectors". What would be desirable are more efficient methods and systems for determining parameters for each of a plurality of vectors in a cardiac rhythm management system.

SUMMARY

The present disclosure relates generally to systems and methods for determining a plurality of parameters for each of a plurality of vectors in an implantable medical device system. Some systems and methods of the present disclosure may relate to selecting one or more of the vectors based on determined parameters for delivery of electrical stimulation therapy by the implantable medical device. For example, and in some instances, the present disclosure describes systems and methods for efficiently determining one or more parameters for a vector of an implantable medical device system and for identifying one or more suitable vectors for sensing cardiac electrical data and/or delivering electrical stimulation therapy based on one or more of the determined parameters. Reducing the time required to determine the one or more parameters for each vector can help reduce procedure time for implanting and/or configuring an implantable medical device, which can reduce costs and/or improve patient comfort.

In one example, a method of determining parameters for each of a plurality of vectors of a multi-electrode implantable medical device may include outputting one or more pacing pulses during a first period of time using a first vector of the multi-electrode implantable medical device at a first pacing voltage, wherein the first vector uses a first pair of electrodes of the multi-electrode implantable medical device. A first parameter may be determined during the first period of time, and a measure related to the first parameter for the first vector may be stored in a memory. One or more pacing pulses may then be outputted during a second period of time using the first vector at a second pacing voltage. A second parameter may be determined during the second period of time, wherein the second parameter is different from the first parameter. A measure related to the second parameter for the first vector may also be stored in the memory.

In another example, a method for determining parameters for each of a plurality of vectors of a multi-electrode implantable medical device may include outputting one or more pacing pulses during a first period of time using a first vector of the multi-electrode implantable medical device at a first pacing voltage, wherein the first vector uses a first pair of electrodes of the multi-electrode implantable medical device. A presence of phrenic stimulation and/or an impedance between the first pair of electrodes during the first period of time may be determined, and a measure related to the presence of phrenic stimulation and/or a measure related to the impedance between the first pair of electrodes for the first vector may be stored. Next, one or more pacing pulses may be outputted during a second period of time using the first vector at a second pacing voltage, wherein the second pacing voltage may be less than the first pacing voltage, and it may be determined whether capture of the heart occurs during the second period of time. A measure related to whether capture occurs for the first vector may then be stored.

In yet another example, a system for determining parameters for each of a plurality of vectors of a multi-electrode implantable medical device that includes three or more implantable electrodes, a pulse generator for generating pacing pulses, a vector selector for selecting between two or more vectors for applying the pacing pulses from the pulse generator, and a controller coupled to the pulse generator and the vector selector. The controller may be configured to: select a first vector using the vector selector, output one or more pacing pulses during a first period of time using the first vector at the first pacing voltage, determine a presence of phrenic stimulation and/or an impedance using the first vector during the first period of time, store a measure related to the presence of phrenic stimulation and/or a measure related to the impedance for the first vector, output one or more pacing pulses during a second period of time using the first vector at a second pacing voltage, wherein the second pacing voltage is less than the first pacing voltage, determine whether capture occurs during the second period of time, store a measure related to whether capture occurs for the first vector, select a second vector using the vector selector, output one or more pacing pulses during a $2^{nd}$ first period of time using the second vector at the first pacing voltage, determine a presence of phrenic stimulation and/or an impedance using the second vector during the $2^{nd}$ first period of time, store a measure related to the presence of phrenic stimulation and/or a measure related to the impedance for the second vector, output one or more pacing pulses during a $2^{nd}$ second period of time using the second vector at the second pacing voltage, determine whether capture occurs during the $2^{nd}$ second period of time, and store a measure related to whether capture occurs for the second vector. In some cases, the first period of time and the $2^{nd}$ first period of time may precede the second period of time and the $2^{nd}$ second period of time, while in other instances, the first period of time and the second period of time may both precede the $2^{nd}$ first period of time and the $2^{nd}$ second period.

In some instances, two or more parameters may be sequentially determined for each vector. When so provided, and in some cases, when a particular parameter for a vector is determined to be undesirable (e.g. a parameter is out of a predefined range, there is presence of an undesirable response such as phrenic nerve stimulation or no capture at a supracapture voltage, etc.), then further processing to determine any remaining parameters for that vector may be terminated. Moreover, in some cases, less than all of the parameters may be determined for two or more of the vectors, and a user may be given the option to select and/or de-select the vectors based on the determined parameters. Then, some or all of the remaining parameters may be determined for the selected vectors.

The above summary is not intended to describe each embodiment or every implementation of the present disclosure. Advantages and attainments, together with a more complete understanding of the disclosure, will become apparent and appreciated by referring to the following description and claims taken in conjunction with the accompanying drawings.

BRIEF DESCRIPTION OF THE DRAWINGS

The disclosure may be more completely understood in consideration of the following description of various illustrative embodiments in connection with the accompanying drawings, in which:

FIG. 5 is a graphical illustration of a table that the implantable medical system of FIG. 1 may generate for a user that includes the determined vector parameters;

Figure 1:
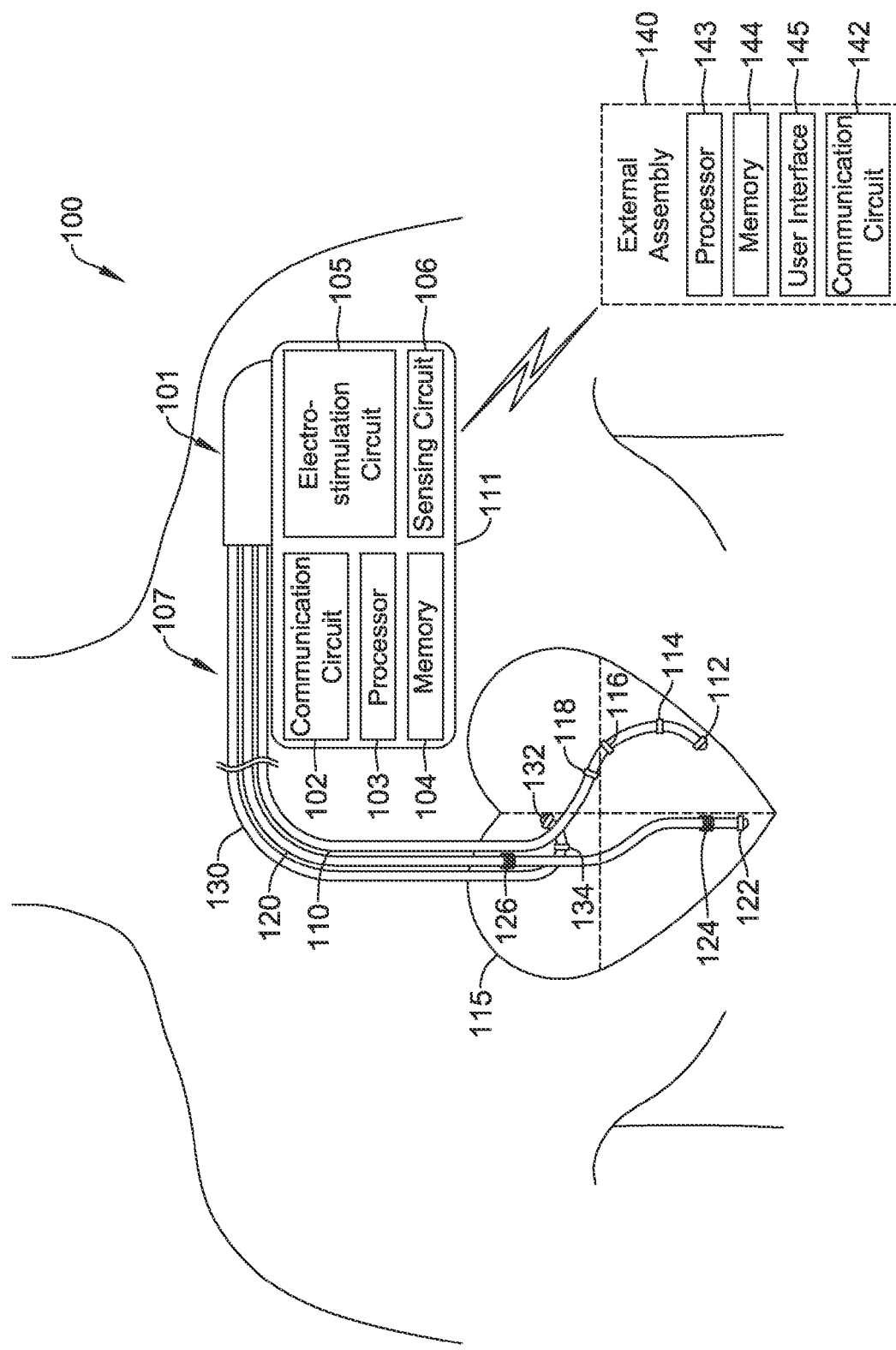
FIG. 1 is a schematic view of an illustrative implantable medical system.

While the disclosure is amenable to various modifications and alternative forms, specifics thereof have been shown by way of example in the drawings and will be described in detail. It should be understood, however, that the intention is not to limit the disclosure to the particular illustrative embodiments described. On the contrary, the intention is to cover all modifications, equivalents, and alternatives falling within the spirit and scope of the disclosure.

DESCRIPTION

The following description should be read with reference to the drawings in which similar elements in different drawings are numbered the same. The description and the drawings, which are not necessarily to scale, depict illustrative embodiments and are not intended to limit the scope of the disclosure.

A normal, healthy heart induces contraction by conducting intrinsically generated electrical signals throughout the heart. These intrinsic signals cause the muscle cells or tissue of the heart to contract. This contraction forces blood out of and into the heart, providing circulation of the blood throughout the rest of the body. However, many patients suffer from cardiac conditions that affect this contractility of their hearts. For example, some hearts may develop diseased tissues that no longer conduct intrinsic electrical stimulation signals. In other examples, diseased tissue may not conduct the intrinsic signals as quickly as healthy tissue, thereby de-synchronizing the contraction of the heart. For example, portions of the heart muscle may contract earlier or later than other muscle cells of the heart due to the different conductivity of the heart tissue with respect to the intrinsic electrical signals. This un-coordinated contraction can result in a decrease in the flow of blood throughout the rest of the body, causing various health problems.

A number of implantable medical device (IMD) systems have been developed to assist such diseased hearts. These IMD systems may include electrodes implanted on or within the heart of the patient. The IMD systems may output/deliver electrical stimulation therapy to the heart through these electrodes. The output/delivered electrical stimulation therapy may replace or assist the intrinsically generated electrical signals in causing the contraction of the heart. One type of electrical stimulation therapy is termed cardiac resynchronization therapy (CRT). In general, CRT includes outputting/delivering electrical stimulation pulses or therapy to a heart, sometimes referred to as "pacing" and "pacing pulses," in order to ensure that all portions of the heart contract in a normal, synchronous manner.

Some IMD systems for delivering CRT include multiple electrodes. However, these IMD systems may only use a portion of these electrodes for sensing cardiac electrical signals or for delivering electrical stimulation therapy at any given time. For example, some IMD systems may use a configuration of two electrodes, which may be termed a "vector," in delivering electrical stimulation therapy, with one electrode acting as a cathode and one electrode acting as an anode. Accordingly, each IMD system generally has numerous potential vectors via which the IMD system may sense cardiac electrical activity and/or deliver electrical stimulation therapy. However, not all of these vectors may be suitable for sensing cardiac electrical activity or delivering electrical stimulation therapy. Additionally, even of the suitable vectors, certain of the suitable vectors may be more desirable for sensing cardiac electrical activity and/or delivering electrical stimulation therapy than others of the suitable vectors.

Many physiological and physical factors can affect which vectors in an IMD system implanted in a given heart will be suitable or more desirable for sensing cardiac electrical activity or delivering electrical stimulation therapy to the heart. For example, such physiological and physical factors may affect the impedance, capture threshold, phrenic nerve stimulation, and electrical delay of each particular vector. Generally, vectors with impedances in a particular range are generally more desirable than vectors with impedances outside of that range. For example, vectors with too low of impedance may use relatively more power when a system delivers electrical stimulation therapy, thereby decreasing battery life at a faster rate than delivering electrical stimulation therapy via vectors with relatively higher impedances. However, too high of impedances for vectors may indicate that such vectors are not making good contact with the myocardium or other tissue, which can result in reduced effectiveness of electrical stimulation delivered via such vectors. The specific desirable impedance range may be determined based on a number of specific hardware factors. Capture thresholds are measures of a minimum voltage of the delivered electrical stimulation needed to capture the heart, which causes the heart to contract in response to the electrical stimulation. Vectors with relatively lower capture thresholds generally require less power over time to deliver effective electrical stimulation therapy than vectors with relatively higher capture thresholds. As many IMD systems are not easily accessible for battery replacement or recharging, power consumption can be an important design consideration.

Phrenic nerve stimulation is another parameter that can be used to determine suitability or desirability of vectors for delivering electrical stimulation. A presence of phrenic nerve stimulation indicates that delivering electrical stimulation via the vector results in stimulation of a patient's phrenic nerve, which can be uncomfortable for a patient. Electrical delay is another parameter useful in assessing suitability or desirability of a vector. For example, vectors with longer electrical delay may be more desirable for delivering electrical stimulation therapy to the heart because delivering electrical stimulation via vectors with relatively longer electrical delays may help produce a more synchronous cardiac contraction.

Whether at the time of implantation or during follow-up visits, it is often desirable to determine the suitability of vectors of an IMD system for sensing cardiac electrical activity or delivering electrical stimulation therapy. However, IMD systems with multiple electrodes have numerous available vectors through which the IMD system can sense cardiac electrical activity and/or deliver electrical stimulation therapy. Because of the numerous available vectors, and because determining each of the aforementioned parameters takes some length of time, assessing all potential vectors can take an extended period of time. This can cause a strain on the patient and can consume limited hospital and physician resources. This disclosure describes systems and techniques for reducing the amount of time to assess vectors and find suitable or desirable vectors for sensing cardiac electrical activity and/or delivering electrical stimulation therapy in an IMD system.

FIG. 1 is a schematic view of an illustrative implantable medical system. FIG. 1 illustrates generally an example of a system 100 that can include an implantable medical device 101. Implantable medical device 101 can be coupled to one or more electro-stimulation electrodes, which can be carried by one or more implantable leads, such as implantable leads 110, 120, and 130. Implantable leads 110, 120, and 130 can be configured to receive or sense cardiac electrical signals from heart 115. In some cases, implantable medical device 101 can include a hermetically-sealed or similar housing 111. Housing 111 can include titanium or another biocompatible material, such as one or more other conductive materials.

In some instances, the electro-stimulation electrodes may be provided by a leadless pacemaker (LCP), which may be in communication with other LCP's and/or with another implantable medical device 101. The use of an LCP may reduce or eliminate the need for one or more of the implantable leads 110, 120 and 130, as desired.

Generally, implantable medical device 101 may include an electro-stimulation or pulse generator device. Accordingly, in some examples, implantable medical device 101 may include one or more of a pacemaker, a defibrillator, an implantable monitor, a drug delivery device, a cardiac resynchronization therapy (CRT) device, a neural stimulation device, and/or one or more other implantable assemblies configured to monitor a person or configured to provide one or more treatments to the person. Examples of such monitoring or treatment can include delivering electrical stimulation therapy to tissues such as cardiac tissue, or electrical monitoring of muscular or cardiac activity. In one example, implantable medical device 101 can include an external medical device, such as a pacing system analyzer, programmer recorder monitor, or other external medical device that can be used to configure a system of implantable leads. In some cases, implantable medical device 101 may include a subcutaneous Implantable Cardioverter-Defibrillator (S-ICD) and/or a subcutaneous pacemaker.

In the example of FIG. 1, implantable medical device 101 can be coupled to heart 115, or other body tissue, such as via electrode system 107, epicardial electrodes, or external (e.g., skin-patch) electrodes. In the system of FIG. 1, electrode system 107 includes at least one lead and at least one electro-stimulation electrode for each lead. FIG. 1 shows an example in which there are three implantable leads 110, 120, and 130. In the example of FIG. 1, implantable lead 110 can be configured for use in association with a left ventricle of the heart 115. For example, implantable lead 110 can be sized and shaped to allow insertion into a coronary sinus and intravascular advancement such as to put at least one electro-stimulation electrode in association with the left ventricle of heart 115. In some examples, implantable lead 110, or any of leads 110, 120, or 130, can be a multipolar lead, a bi-polar lead, a unipolar lead, or any other type of lead. Accordingly, implantable lead 110 may include a plurality of electro-stimulation electrodes and corresponding conductors connecting such electrodes with implantable lead 110. In an example, implantable lead 110 can include four discrete electro-stimulation electrodes, such as: tip electrode 112, first ring electrode 114, second ring electrode 116, and third ring electrode 118. In an example, electro-stimulation electrodes 114, 116, and 118 can be located near a distal portion of implantable lead 110. Each of electro-stimulation electrodes 114, 116, and 118 can be separated by electrically insulating material, thus electrically isolating the individual electro-stimulation electrodes. Each of the four left ventricular electro-stimulation electrodes 112, 114, 116, and 118 can correspond to a unique electrical conductor and can be individually addressable by sensing circuit 106 or electro-stimulation circuit 105 contained within implantable medical device 101.

In the example shown in FIG. 1, implantable lead 120 can include tip electrode 122, first coil electrode 124, and second coil electrode 126. As generally shown in FIG. 1, implantable lead 120 can, in one example, be inserted into the right atrium and right ventricle of heart 115 so that first coil electrode 124 is positioned in the right ventricle and second coil electrode 126 is positioned in the right atrium. Likewise, in the example of FIG. 1, implantable lead 130 can include tip electrode 132 and ring electrode 134. As generally shown in FIG. 1, implantable lead 130 can be configured for insertion into the right atrium of the heart 115.

The physical illustration of implantable leads 110, 120, and 130 provided in FIG. 1 is an illustrative non-limiting example only. Other systems may include leads positioned differently with respect to heart 115. Additionally, other systems may have differing numbers of electro-stimulation electrodes, and the positioning of the electro-stimulation electrodes on the leads may differ. Other systems may also include more or less implantable leads. In a system that uses strictly LCPs, no leads may be required or even desired. In general, the systems and techniques of the present disclosure are amenable to any system including a plurality of electrodes that are configurable into a plurality of vectors, regardless of specific implant locations or electrode placement or numbers.

In one example, implantable medical device 101 can include a communication circuit 102, processor circuit 103, memory circuit 104, electro-stimulation circuit 105, and sensing circuit 106. Processor circuit 103 and memory circuit 104 can be used to control the operation of implantable medical device 101. For example, processor circuit 103 can be configured to detect a cardiac condition, such as by using the sensing circuit 106 or another physiological sensor, and to respond to the detected cardiac condition, such as by causing electro-stimulation circuit 105 to deliver electrical stimulation to heart 115 via one or more electrodes. Memory circuit 104 can include one or more parameters, such as for various pacing and sensing modes, test procedures or the like. Memory circuit 104 can be configured to store physiological data, such as data concerning the condition of heart 115. Memory circuit 104 can also be configured to store device data, such as data about a status of a test or a test result. In one example, implantable medical device 101 can use electro-stimulation circuit 105 or sensing circuit 106 to interface with electrode system 107. Electro-stimulation circuit 105 or sensing circuit 106 can be configured to generate an electro-stimulation signal to provide electrical stimulation therapy to heart 115, for example by using energy stored in a battery (not shown) that is stored within implantable medical device 101. Electro-stimulation circuit 105 or sensing circuit 106 can be electrically coupled to electrode system 107. For example, electrical stimulation can be transmitted from electro-stimulation circuit 105 to heart 115 via electrode system 107. Likewise, sensing circuit 106 may receive signals from electrode system 107. Communication circuit 102 can be configured to establish a data communication link between implantable medical device 101 and, for example, external assembly 140.

In some instances, implantable medical device 101 can be configured to perform vector assessments. For example, processor circuit 103 can cause electro-stimulation circuit 105 to deliver electrical stimulation via some or all of the vectors created by pairs of electro-stimulation electrodes connected to implantable leads 110, 120, and 130. Sensing circuit 106 may detect various signals and/or parameters during the vector assessment and store the detected signals and/or parameters in memory circuit 104. In some cases, processor circuit 103 may communicate the detected signals and/or parameters to external assembly 140, via communication circuit 102. Additionally, external assembly 140 may be configured to receive detected signals and/or parameters and display them with user interface 145.

Implantable medical device 101 can be configured to communicate (wired or wirelessly) via communication circuit 102 with a local or remote external device, such as external assembly 140. This can include using an RF, optical, acoustic, conductive, or other communication link. External assembly 140 can be a portion or part of a patient management system. In one example, external assembly 140 can communicate with one or more remote clients, such as web-based clients, or can be communicatively coupled to one or more servers, which can include medical and patient databases.

In some cases, external assembly 140 can include communication circuit 142, processor circuit 143, memory circuit 144, or user interface 145. In one example, communication circuit 142 can include inductive coils or radio frequency telemetry circuitry, and can be configured to communicate with implantable medical device 101. Processor circuit 143 and memory circuit 144 can be used to interpret information received from user interface 145, or can be used to determine when to use communication circuit 142 to exchange information with implantable medical device 101. In one example, processor circuit 143 and memory circuit 144 can be used to initiate a vector assessment controlled at least in part by external assembly 140 using electrode system 107. External assembly 140 can be used to perform vector assessments using electrode system 107 and can be configured to display results such as by user interface 145. In some cases, external assembly 140 is not used and it is implantable medical device 101 that is configured to perform vector assessments using electrode system 107

When used, external assembly 140 can be an adjunct (e.g., non-implantable) external assembly. In one example, external assembly 140 can include the features of implantable medical device 101 described above and below, such that external assembly 140 can be configured to be directly or indirectly coupled to the electrode system 107. For example, external assembly 140 can be configured to assess each of the potential vectors resulting from all the various combinations of electro-stimulation electrodes 112, 114, 116, 118, 122, 124, 126, 132, and 134. External assembly 140 may be able to perform an assessment by utilizing a power source (not shown) to deliver electrical stimulation pulses to electrode system 107. External assembly 140 may be equipped with one or more algorithms that automatically select one or more of the assessed vectors and configures implantable medical device 101 with the selected vectors. In other examples, a user, such as a physician or other medical professional, may view results of the assessment and provide selections of one or more vectors. These selected vectors may be communicated to implantable medical device 101 via communication circuit 142. By using external assembly 140 to perform vector assessments, implantable medical device 101 may conserve power.

User interface 145 of external assembly 140 can include, but is not limited to, a keyboard, a mouse, a light pen, a touch-screen, a display screen, a printer, or an audio speaker. In one example, user interface 145 can be configured as a full color, high definition graphical display, such as using an LCD computer monitor. In another example, user interface 145 can be configured for use as a monochromatic display, such as using a CRT monitor to display text. In some examples, user interface 145 can be configured to interactively present a graphical representation of vector assessments to a user. In other examples, user interface 145 can be configured to interactively present a text-based representation of vector assessments. For example, user interface 145 may present information received from processor circuit 143 and/or memory circuit 144, or, alternatively, from processor circuit 103 and/or memory circuit 104, such as through communication circuits 102 and 142.

Figure 2:
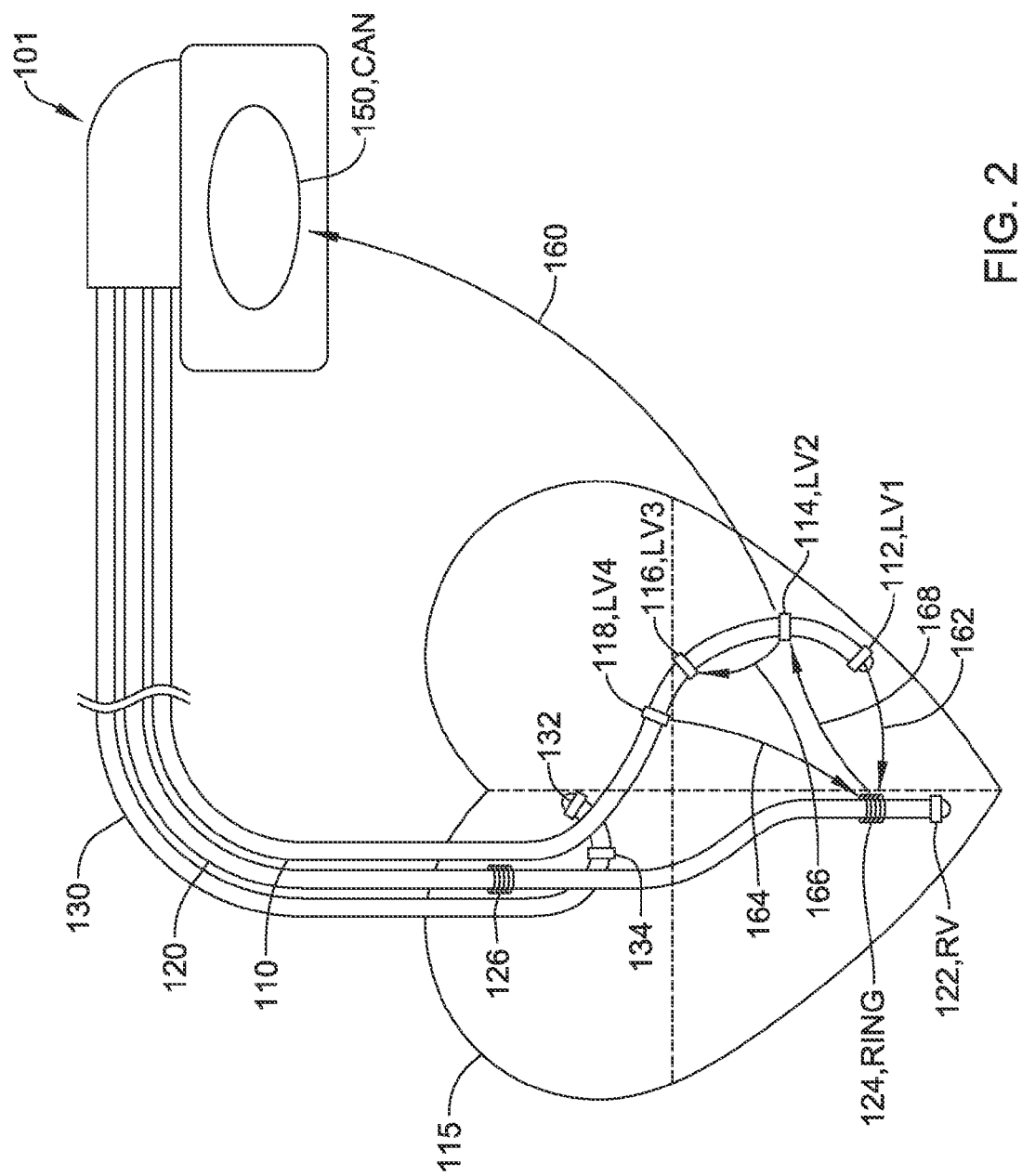
FIG. 2 is a schematic diagram of the implantable medical system of FIG. 1 showing various illustrative vectors.

FIG. 2 is a schematic diagram of the implantable medical system of FIG. 1 showing some exemplary vectors. As described with respect to FIG. 1, each pair of electro-stimulation electrodes of implantable medical device 101 may be considered a "vector". For each pair of electro-stimulation electrodes, a first one of the electro-stimulation electrodes is a cathode electrode and a second one of the electrodes is an anode electrode. In each of the illustrated example vectors, the arrow of each vector points to the anode electrode and the base of each arrow points to the cathode electrode. Although each vector is drawn as an arrow indicating a pathway, the vector only represents a general flow of electrical stimulation propagation when electrical stimulation is delivered via the particular vector. The exact pathway of electrical stimulation propagation will depend on many factors including physiological and physical system factors.

In some examples, implantable medical device 101 further includes a "can" electrode 150, as shown in FIG. 2. FIG. 2 further illustrates example vectors 160, 162, 164, 166, and 168. In FIG. 2, electro-stimulation electrodes 112, 114, 116, 118, 122, 124, and 150 are also labeled as LV1, LV2, LV3, LV4, RV, RING, and CAN (sometimes referred to in the art as Q), respectively, which are terms sometimes used in the art. Vector 160 represents the pair of the CAN electrode and the LV2 electrode, where the CAN electrode is an anode electrode and the LV2 electrode is a cathode electrode. The other vectors 162, 164, 166, and 168 all represent examples of vectors of implantable medical device 101. It should be understood that any combination of electro-stimulation electrodes may represent a unique vector. Additionally, each pair of electro-stimulation electrodes can actually produce two vectors because either of the pair of electro-stimulation electrodes can be the cathode electrode or the anode electrode. Table 1 below lists all of the possible vectors of implantable medical device 101 comprising the RV, LV1, LV2, LV3, LV4, and CAN electrodes. The totality of possible vectors of implantable medical device 101 would further comprise combinations including electrodes 126, 132, 134, and RING. However, it should be understood that in other implantable medical device systems, particularly those with differing amounts of electro-stimulation electrodes, the number of vectors of the system may be different. The example techniques described herein may be applicable to any such system including multiple electro-stimulation electrodes.

TABLE 1

| Vector | Electrode Combination (Cathode Electrode → Anode Electrode) |
|---|---|
| Vector 1 (164) | LV1 → RV |
| Vector 2 | LV1 → LV4 |
| Vector 3 | LV1 → LV3 |
| Vector 4 | LV1 → LV2 |
| Vector 5 | LV1 → CAN |
| Vector 6 (184) | LV2 → RV |
| Vector 7 | LV2 → LV4 |
| Vector 8 | LV2 → LV3 |
| Vector 9 | LV2 → LV1 |
| Vector 10 (160) | LV2 → CAN |
| Vector 11 (182) | LV3 → RV |
| Vector 12 | LV3 → LV4 |

TABLE 1-continued

| Vector | Electrode Combination (Cathode Electrode → Anode Electrode) |
|---|---|
| Vector 13 (166) | LV3 → LV2 |
| Vector 14 | LV3 → LV1 |
| Vector 15 | LV3 → CAN |
| Vector 16 (162) | LV4 → RV |
| Vector 17 | LV4 → LV1 |
| Vector 18 | LV4 → LV2 |
| Vector 19 | LV4 → LV3 |
| Vector 20 | LV4 → CAN |
| Vector 21 | RV → LV1 |
| Vector 22 | RV → LV2 |
| Vector 23 (168) | RV → LV3 |
| Vector 24 | RV → LV4 |
| Vector 25 | RV → CAN |
| Vector 26 | CAN → RV |
| Vector 27 | CAN → LV1 |
| Vector 28 | CAN → LV2 |
| Vector 29 | CAN → LV3 |
| Vector 30 | CAN → LV4 |

Figure 3:
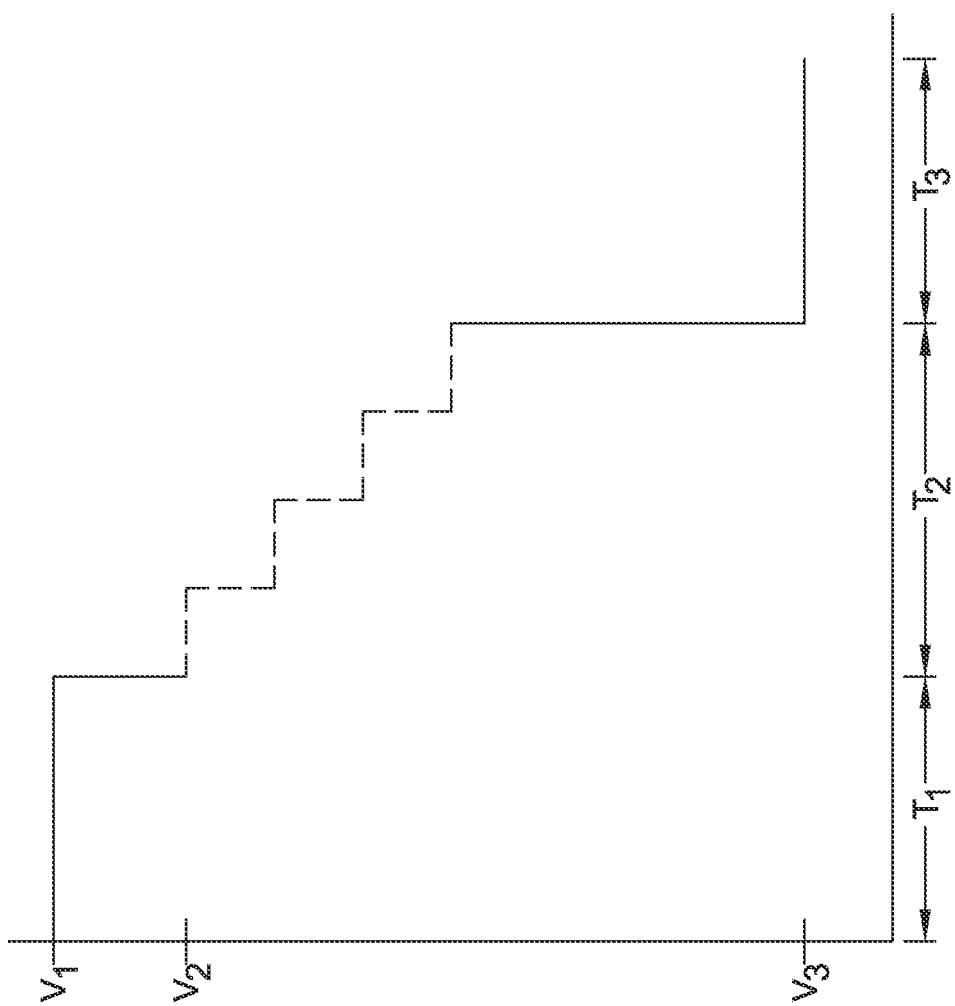
FIG. 3 is a graphical illustration of voltage amplitudes and time periods that may be used by the implantable medical system of FIG. 1 in performing a vector assessment.

FIG. 3 is a graphical representation of an example stepwise method that the system of FIG. 1 may perform for assessing a vector. In FIG. 3, the y-axis represents voltage amplitude of delivered electrical stimulation and the x-axis represents time. In one example operation, implantable medical system 100 may begin a vector assessment by delivering electrical stimulation (e.g. a plurality of pacing pulses) to heart 115 at a first voltage amplitude, V1, for a first period of time, T1. In some examples, voltage amplitude V1 may generally be chosen as to induce cardiac contraction in a majority of patients. In some cases, the amplitude V1 may be considered a supracapture voltage. After delivering electrical stimulation therapy, system 100 may further determine one or more parameters for the particular vector. For example, system 100 may determine whether the delivered electrical stimulation did, in fact, cause a contraction of heart 115 (i.e. capture).

After determining that the delivered electrical stimulation caused a contraction of heart 115, system 100 may determine and store a template, termed an "evoked response template", which reflects the electrical activity of heart 115 in response to the delivered electrical stimulation, e.g. the "evoked response". If system 100 did not detect that the delivered electrical stimulation caused a contraction of heart 115, system 100 may skip the current vector and begin a new assessment of a different vector. In other examples, system 100 may deliver electrical stimulation therapy with a voltage amplitude higher than V1, and may continue to increase the delivered voltage amplitude until system 100 detects that the delivered electrical stimulation caused a contraction of heart 115 or a maximum voltage has been reached. If system 100 reaches the maximum voltage amplitude without detecting that the delivered electrical stimulation caused a contraction of heart 115, system 100 may skip the assessment of the current vector and begin an assessment with a new vector.

During time T1, system 100 may additionally determine one or more parameters other than whether the delivered electrical stimulation at voltage amplitude V1 caused a contraction of the heart (or other voltage levels in case the delivered electrical stimulation at voltage V1 did not cause a contraction of heart 115). For example, during time T1, system 100 may further determine whether the delivered electrical stimulation caused phrenic nerve stimulation. Accordingly, some examples of system 100 may include a device or technique for determining a presence of phrenic nerve stimulation. For example, system 100 may include an accelerometer connected to implantable medical device 101 or external assembly 140. After delivering electrical stimulation therapy, system 100 may determine a presence of phrenic nerve stimulation based on the received signal from the accelerometer. For example, stimulating the phrenic nerve of a patient may cause a portion of the patient's body to spasm, which may result in an increased signal level or a distinctive signal morphology in the signal from the accelerometer. Other examples of system 100 may be able to detect a presence of phrenic nerve stimulation based on a particular morphology of the evoked response of heart 115. In some cases, a physician may input for each pacing pulse whether phrenic stimulation was observed.

In other examples, system 100 may additionally determine whether delivered electrical stimulation causes phrenic nerve stimulation at different voltage amplitudes. For example, as discussed below, system 100 may be configured to deliver electrical stimulation therapy at voltage amplitudes other than at voltage amplitude V1, during time T2. At each of these additional voltage amplitudes, system 100 may also determine whether the delivered electrical stimulation caused phrenic nerve stimulation. System 100 may store the lowest voltage amplitude at which system 100 determines the electrical stimulation therapy caused phrenic nerve stimulation.

System 100 may further determine an impedance of the vector during time T1. In order to determine the impedance for the assessed vector, system 100 may deliver a voltage pulse or other electrical stimulation therapy, to a first electro-stimulation electrode of the vector and measure a current flow between the first and second electro-stimulation electrodes of the vector. Using Ohm's Law, Z=V/I, system 100 may determine an impedance for each vector. Alternatively, system 100 may deliver a current pulse to a first electro-stimulation electrode of a vector and measure the resulting voltage differential between the first and second electro-stimulation electrodes of the vector and use Ohm's Law to determine impedance. In some examples, system 100 may use one or more of the delivered pacing pulses as the delivered voltage or current pulse in order to determine the impedance for the vector.

After time period T1, system 100 may deliver different electrical stimulation therapy during time T2 in order to determine, for example, a capture threshold, e.g. an approximate minimum voltage amplitude of the delivered electrical stimulation required to cause a contraction of heart 115. In the example shown, system 100 may deliver electrical stimulation therapy (e.g. pacing pulses) at a second voltage amplitude, V2, which is less than voltage amplitude V1. System 100 may determine whether the delivered electrical stimulation caused a contraction of heart 115, only this time at voltage amplitude V2.

If system 100 determines that the delivered electrical stimulation at voltage amplitude V2 did cause a contraction of heart 115, system 100 may proceed to time period T3 of FIG. 3. In such cases, voltage amplitude V2 may be set to a voltage amplitude that is deemed to be an acceptable electrical stimulation voltage for subsequent pacing (e.g. 2.5 V), so long as it captures the heart.

In some instances, however, system 100 may be configured to deliver additional electrical stimulation therapy at decreasing voltage amplitudes during time period T2. For example, system 100 may be configured to decrease the voltage amplitude by a predetermined amount, such as 0.1V, 0.2V, 0.25V, 0.5V, 0.75V, 1V, or any other suitable voltage amount. Accordingly, after delivering electrical stimulation therapy at a voltage amplitude less than V2, system 100 may additionally determine whether the delivered electrical stimulation at the current voltage amplitude caused a contraction of heart 115. System 100 may be configured to continually deliver electrical stimulation at decreasing voltage amplitudes until determining that delivered electrical stimulation at a current voltage amplitude failed to cause a contraction of heart 115. The dashed lines of FIG. 3 are meant to represent that various size voltage steps may be used in delivering electrical stimulation and that different number of steps may be used by system 100 in determining a capture threshold. After determining that delivered electrical stimulation at the current voltage amplitude failed to cause a contraction of heart 115, system 100 may determine that the previous voltage amplitude is the capture threshold of the vector. While a step down capture threshold technique is shown in FIG. 3, it is contemplated that any suitable capture threshold technique may be used, as desired.

In some instances, if system 100 determines that the delivered electrical stimulation did not cause a contraction of heart 115 at the initial voltage V2, system 100 may deliver additional electrical stimulation at a voltage amplitude above V2 but less than V1. For example, system 100 may be configured to increase the voltage amplitude by a predetermined amount, such as 0.1V, 0.2V, 0.25V, 0.5V, 0.75V, 1V, or any other suitable voltage amount. System 100 may continue to deliver electrical stimulation therapy at increasing voltage amplitudes, each time increasing the voltage amplitude by a predetermined amount, until system 100 determines that the delivered electrical stimulation at a current voltage amplitude caused a contraction of heart 115. Note this operation is in contrast the dashed lines in the example of FIG. 3. In such an example, an accurate graph may include steps in voltage during time period T2 that are increasing, as opposed to decreasing. System 100 may then determine that the current voltage amplitude is the capture threshold of the vector.

In the example shown, after determining a capture threshold, system 100 may deliver electrical stimulation therapy at a third voltage amplitude, V3, during a third time period, T3. In some examples, V3 may be a low voltage amplitude such as 1V, 0.75V, 0.5V, 0.25V, 0.1V, or any other suitable low voltage amplitude. In some examples, V3 may be 0V, such that system 100 is not delivering electrical stimulation therapy during the third time period, T3. In still other examples, system 100 may confirm that the delivered electrical stimulation at voltage amplitude V3 does not result in causing heart 115 to contract.

After determining that heart 115 does not contract in response to the delivered electrical stimulation at voltage amplitude V3, system 100 may determine one or more additional parameters of the current vector. For example, system 100 may determine an RV-LV delay for the vector. In order to measure RV-LV delay, system 100 may deliver electrical stimulation to a first electro-stimulation electrode of the current vector and determine an elapsed time before detecting the delivered electrical stimulation at the second electro-stimulation electrode of the current vector. In some examples, this determined delay may be called the paced delay. In other examples, system 100 may measure a difference in time when system 100 detects a QRS wave of an intrinsic depolarization of heart 115 at a first electro-stimulation electrode of the vector and when system 100 detects that same depolarization wave at a second electro-stimulation electrode of the vector. In some examples, this determined delay may be called the intrinsic delay. From this, the system 100 may determine the RV-LV delay for the vector. In still other examples, system 100 may determine a difference between times when system 100 detects a QRS wave of an intrinsic depolarization of heart 115 at surface electrodes, for example skin-patch electrodes positioned on the patient, connected to system 100 and when system 100 detects the same depolarization wave at a first electrostimulation electrode implanted within the patient. System 100 may determine such a difference in time to be, for example, a QLV delay for the vector.

In other examples, system 100 may determine an RV-LV delay at times other than during time T3. For example, system 100 may determine an RV-LV delay during time T1. During time T1, system 100 may be delivering electrical stimulation therapy that captures the heart and may determine a delay based on the delivered pacing pulses. In other examples, system 100 may determine an RV-LV delay before time T1 or after time T3. In such examples, system 100 may deliver electrical stimulation via an electrode in the right ventricle and may sense for the delivered electrical stimulation at one or more left ventricle electrodes. In some examples, system 100 may be connected to a pacing-dependent patient. Such patients may require delivered electrical stimulation from system 100 in order to cause heart 115 to contract. In such systems, during any of times T2 or T3, system 100 may deliver electrical stimulation specifically to cause heart 115 to contract. For example, if delivered electrical stimulation therapy has failed to cause the heart to contract, system 100 may deliver a safety pulse that is designed to capture heart 115 and cause it to contract. In such examples, system 100 may use the delivered safety pulse in determining an RV-LV delay.

In some instances, during time T3, system 100 may determine an intrinsic R-wave amplitude. For example, system 100 may detect a QRS wave of an intrinsic depolarization of heart 115 and may measure the amplitude of the R-wave of the depolarization. In some examples, system 100 may measure the amplitude of a number of R-waves during time T3. Accordingly, system 100 may determine an average of the determined R-wave amplitudes as the R-wave amplitude of the vector.

Figure 4:
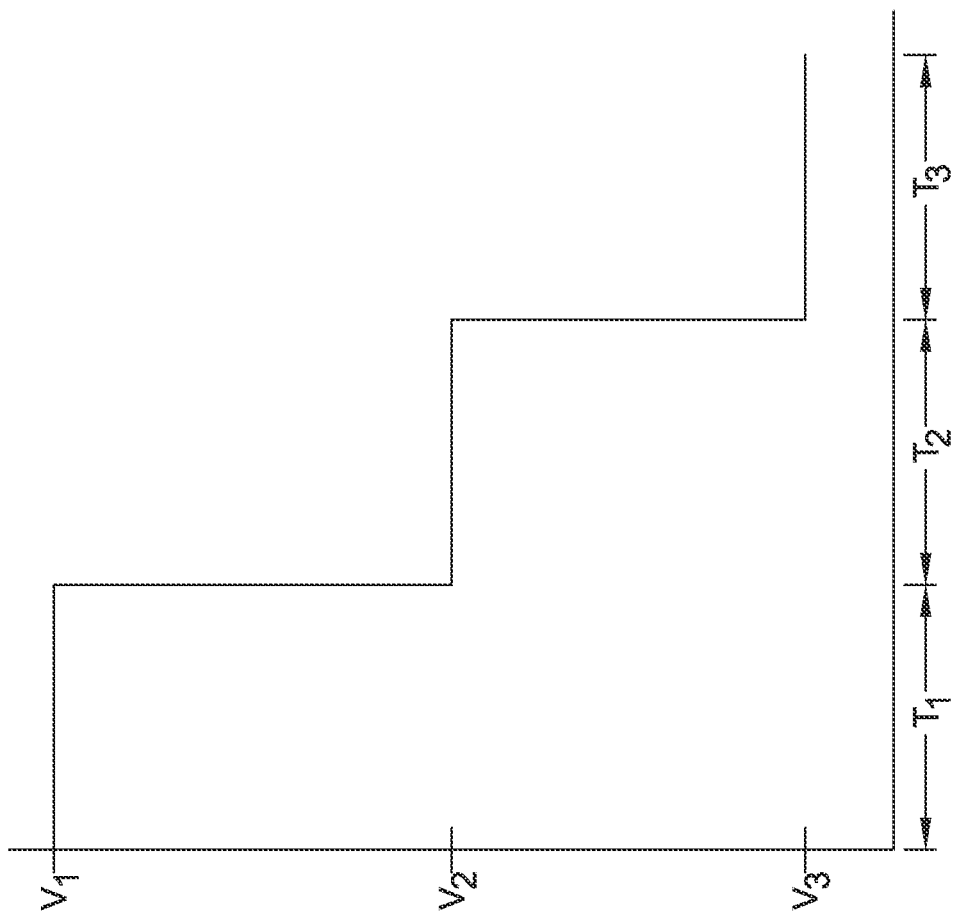
FIG. 4 is a graphical illustration of voltage amplitudes and time periods that may be used by the implantable medical system of FIG. 1 in performing a vector assessment.

FIG. 4 is a graphical representation of another example method that the system of FIG. 1 may perform for assessing a vector. FIG. 4 includes many of the features of FIG. 3. However, the illustrative method of FIG. 4 differs from the illustrative method of FIG. 3 in that the illustrative method of FIG. 4 uses a binary-threshold capture technique as opposed to the step-wise method of FIG. 3. For example, instead of delivering electrical stimulation therapy at a plurality of voltage amplitudes during time T2 in order to determine an approximate voltage amplitude at which loss of capture of heart 115 occurs (e.g. a capture threshold), the method of FIG. 4 only includes a single voltage amplitude at which system 100 determines whether the delivered electrical stimulation caused a contraction of heart 115.

According to the method depicted by FIG. 4, after time period T1, system 100 may deliver electrical stimulation therapy at a second voltage amplitude, V2. While delivering electrical stimulation therapy at voltage amplitude V2, system 100 determines whether the delivered electrical stimulation therapy causes heart 115 to contract. If system 100 determines that the delivered electrical stimulation therapy causes heart 115 to contract, system 100 may determine that the capture threshold is less than or equal to V2. If system 100 determines that the delivered electrical stimulation therapy does not cause heart 115 to contract, system 100 may determine that the capture threshold is greater than V2. After making a determination, system 100 may transition to time period T3 and begin delivering electrical stimulation therapy at voltage amplitude V3, instead of increasing or decreasing the voltage amplitude of the delivered electrical stimulation during time period T2 in order to determine a more accurate capture threshold. Using such a binary-threshold approach, as opposed to the step-wise approach discussed with reference to FIG. 3, may reduce the time needed for system 100 to assess a vector.

Additionally, although each of the determinations of parameters, e.g. presence of phrenic nerve stimulation, impedance, capture threshold, RV-LV delay, R-wave amplitude, etc., has been described with respect to a particular time period, in various examples, system 100 may determine the parameters in different time periods than that shown in FIGS. 3-4. For example, as discussed above, system 100 may additionally determine a presence of phrenic nerve stimulation in time period T2. In some examples, system 100 may additionally determine impedance during time period T2. In still other examples, system 100 may determine impedance during time period T3. Additionally, in some examples, system 100 may determine an evoked response template during time period T2 during the delivery of electrical stimulation that captures heart 115.

Moreover, it is contemplated that the illustrative methods shown in FIGS. 3-4 may be performed sequentially on each of a plurality of vectors. That is, the system 100 may select a first vector and determine parameters during each of time periods T1-T3, and then repeating for each subsequent vector. Alternatively, the system 100 may determine parameters during time period T1 for each of two or more vectors, before moving on to time period T2, and determine parameters during time period T2 on each of the two or more vectors, before moving on to time period T3, and so on.

In general, system 100 may be configured to handle multiple input signals in order to determine the parameters. For example, during time period T1, system 100 may be configured to deliver electrical stimulation therapy (e.g. pacing pulses) and simultaneously receive signals relating to phrenic nerve stimulation, an evoked response, and impedance. In such an example, system 100 may receive as input cardiac electrical signals generated by heart 115 in response to the delivered electrical stimulation. System 100 may simultaneously receive as input sensor signals from an accelerometer. System 100 may additionally simultaneously receive as input a signal used to determine an impedance. Accordingly, system 100 may be configured to determine an impedance from one of the input signals, record an evoked response template from one of the input signals, and determine a presence of phrenic nerve stimulation from one of the input signals, all during time period T1. In some examples, some of the signals used to determine each of the parameters may be the same signal. In other examples, each of the input signals may be received simultaneously, but system 100 may process the input signals and determine the parameters sequentially. In other examples, each of the input signals may be received sequentially, and system 100 may process the input signals and determine the parameters sequentially.

As detailed above, system 100 may include a plurality of vectors. The method described above may be used by system 100 to perform an assessment on each of the vectors of system 100. Accordingly, system 100 may determine a number of parameters for each of a plurality of vectors of system 100. System 100 may further be configured to present the determined parameters to a user, such as through user interface 145.

FIG. 5 illustrates an example output of system 100 to user interface 145. For example, after determining parameters for one or more vectors of system 100, processor circuit 103 or processor circuit 143 may cause user interface 145 to display the determined parameters. In at least one example, processor circuit 103 or processor circuit 143 may cause user interface 145 to display the determined parameters in a table, such as table 400 depicted in FIG. 5. Table 400 may include one or more rows 438, where each row 438 represents a single vector of system 100. Each of the columns of table 400 may represent a parameter of the vectors 438 of system 100. For example, table 400 may include a PS Present column 444. The cells of PS Present column 444 may contain information related to a presence of phrenic nerve stimulation for a corresponding vector 438. In examples where system 100 only determines a presence of phrenic nerve stimulation during time T1 at voltage amplitude V1, PS Present column 444 may include a 'Yes' or a 'No' value in each of its cells indicating whether system 100 determined a presence of phrenic nerve stimulation at voltage amplitude V1. In other examples, where system 100 determines a presence of phrenic nerve stimulation at multiple voltage amplitudes, PS Present column 444 may include a 'No' value in cells corresponding to vectors 438 where system 100 did not determine any presence of phrenic nerve stimulation at any voltage amplitude. PS Present column 444 may include a voltage value and a greater than symbol, e.g. '>', in cells corresponding to vectors 438 where system 100 determined a presence of phrenic nerve stimulation, where the voltage value represents the highest voltage value at which system 100 determined a presence of phrenic nerve stimulation. Other examples may use other values for cells of PS Present column 444 to indicate similar information, e.g. whether system 100 determines a presence of phrenic nerve stimulation for the vector 438 and at what voltages.

The Impedance column 442 may include information relating to the determined impedance for each corresponding vector 438. In some examples, the values of the cells of Impedance column 442 may be expressed in Ohms.

The LV Capture column 446 may include information relating to the determined capture threshold for each corresponding vector 438. In examples where system 100 used the binary-threshold method, if system 100 determined that the delivered electrical stimulation at voltage amplitude V2 captured the heart in a given vector, the corresponding cell of LV Capture column 446 may include a voltage value, V2, expressed in volts, and a less than or equal to than symbol indicating that the capture threshold of the vector is equal to or below voltage value V2. If system 100 determined that the delivered electrical stimulation at voltage amplitude V2 did not capture the heart in a given vector, the corresponding cell of LV Capture column 446 may include a voltage value, V2, and a greater than symbol indicating that the capture threshold of the vector is greater than voltage value V2. In examples where system 100 used the step-wise method, the cells of LV Capture column 446 may include single voltage amplitudes. For example, for a given vector 438, the corresponding cell of LV Capture column 446 may include the lowest voltage value, expressed in volts, at which system 100 determined the delivered electrical stimulation capture heart 115.

RV-LV Timing column 440 may include information relating to the determined RV-LV delay for each vector 438. For example, each cell of RV-LV Timing column 440 may include a value representing an amount of milliseconds that system 100 determined as the RV-LV delay for each vectors 438.

R-Wave Amp column 450 may include information relating to the determined R-wave amplitude of each vector 438. For example, each cell of R-Wave Amp column 450 may include a voltage value indicating a specific voltage that system 100 determined as the R-wave amplitude of each vector 438. In some examples, each cell of R-Wave Amp column 450 may express a voltage value in millivolts.

In some examples, system 100 may allow for a user to input information into system which 100 which may affect the vector assessment. For example, in some examples, system 100 may present one or more input fields to a user through user interface 145. At least one of the input fields may represent a starting voltage value V1. In such examples, a user may enter a particular starting voltage value V1 that system 100 may use when performing a vector assessment. In some examples, system 100 may present a first voltage value Va to the user through user interface 145 and allow the user to edit this first voltage value Va. System 100 may then use the edited or un-edited voltage value Va as voltage value V1 for use in any of the vector assessment techniques described above.

In additional examples, system 100 may present additional input fields. One such input field may be a second voltage value Vb. System 100 may use any input second voltage value Vb as voltage amplitude V2 for use in any of the vector assessment techniques described above. In still other examples, system 100 may additionally display a third voltage value Vc. System 100 may use any input second voltage value Vc as voltage amplitude V3 for us in any of the vector assessment techniques described above. As with the first voltage value Va, system 100 may display preset second and third voltage values Vb and Vc to a user through user interface 145 and allow a user to edit the preset voltage values.

In some examples, system 100 may present a user with an option to choose either a binary-threshold technique or a step-wise threshold technique. Upon receiving a selection of one of the options, system 100 may then employ the selected technique when performing vector assessments. If a user selected the step-wise threshold technique, system 100 may additionally display an input field for a step-voltage. A user may then enter a step-voltage that system 100 may use as the voltage increment by which to increase or decrease the delivered electrical stimulation therapy during time period T2 in order to determine a capture threshold. In other examples, system 100 may display a preset step-voltage in an input field and the user may choose to edit the preset step-voltage to a different step-voltage. System 100 may then use the edited or un-edited step-voltage as the voltage increment by which to increase or decrease the delivered electrical stimulation therapy during time period T2 in order to determine a capture threshold.

In other examples, system 100 may additionally, or alternatively, allow a user to select a first phrenic stimulation determination technique or a second phrenic stimulation determination technique. In such examples, if a user selects a first phrenic stimulation determination technique, system 100 may only determine a presence of phrenic nerve stimulation during time period T1 and voltage amplitude V1. If a user selects a second phrenic stimulation determination technique, system 100 may additionally determine whether phrenic nerve stimulation is present at voltage amplitudes other than voltage amplitude V1. For example, system 100 may continue to determine a presence of phrenic nerve stimulation during time period T2 concurrently with determining a capture threshold.

In some examples, system 100 may additionally, or alternatively, allow a user to select first, second, and third time period lengths, Ta, Tb, and Tc. For example, system 100 may present to a user, through user interface 145, input fields that allow a user to set time periods Ta, Tb, and Tc. System 100 may then use these first, second, and third time periods Ta, Tb, and Tc as time periods T1, T2, and T3 when performing vector assessments. In some examples, the time periods Ta, Tb, and Tc all represent an amount of time in seconds. In other examples, time periods Ta, Tb, and Tc all represent an amount of heartbeats or delivered pacing pulses.

In still other examples, system 100 may additionally, or alternatively, allow a user to select specific vectors of system 100. For example, system 100 may display a table of all vectors of system 100, such as vectors 438 in table 400. System 100 may then receive a selection of one or more vectors. When system 100 performs vector assessments, for example in accordance with the techniques disclosed above, system 100 may only perform vector assessments on the received selected vectors.

Allowing a user to adjust the parameters of the vector assessment of system 100 may allow for many advantages over non-customizable systems. For example, allowing the user to select an amount of time for time periods T1, T2, and T3, whether to perform a binary-threshold or a step-wise threshold capture technique, and on which vectors that system 100 should perform a vector assessment all allow the user to adjust the amount of time taken by system 100 in performing an assessment of a vectors. This allows a user to balance the time taken to determine the various parameters for each of the selected vectors, with the precision of the determined parameters (e.g. a range for a capture threshold as opposed to a specific voltage value). Accordingly, a user may elect to determine general parameters for a few vectors when under great time constraints, yet may perform more thorough analysis of more vectors when time permits.

In some instances, two or more parameters may be determined for each selected vector. When so provided, and in some cases, when a particularly parameter for a vector is determined to be undesirable (e.g. a parameter is out of a predefined range, there is presence of an undesirable response such as phrenic stimulation or no capture at a supracapture voltage, etc.), then further processing to determine any remaining parameters for that vector may be automatically terminated.

Moreover, in some cases, the system 100 may determine less than all of the parameters for each of two or more of the vectors, and a user may be given the option to select and/or select the vectors based on the determined parameters. Some or all of the remaining parameters may be determined for only the selected vectors. In the example shown in FIG. 5, only some of the columns in table 400 may be determined for each of the vectors by system 100, and then the user may be given the option to select which of the vectors to proceed with further processing. Then, some or all of the remaining parameters may be determined for only the selected vectors.

It is also contemplated that while three time periods are shown in FIGS. 3-4, it is contemplated that more or less time periods may be provided. Also, while particular tests are described with reference to particular time periods T1-T3, it is contemplated that the order of the test and/or the order of the time periods may be changed, as desired.

Figure 6:
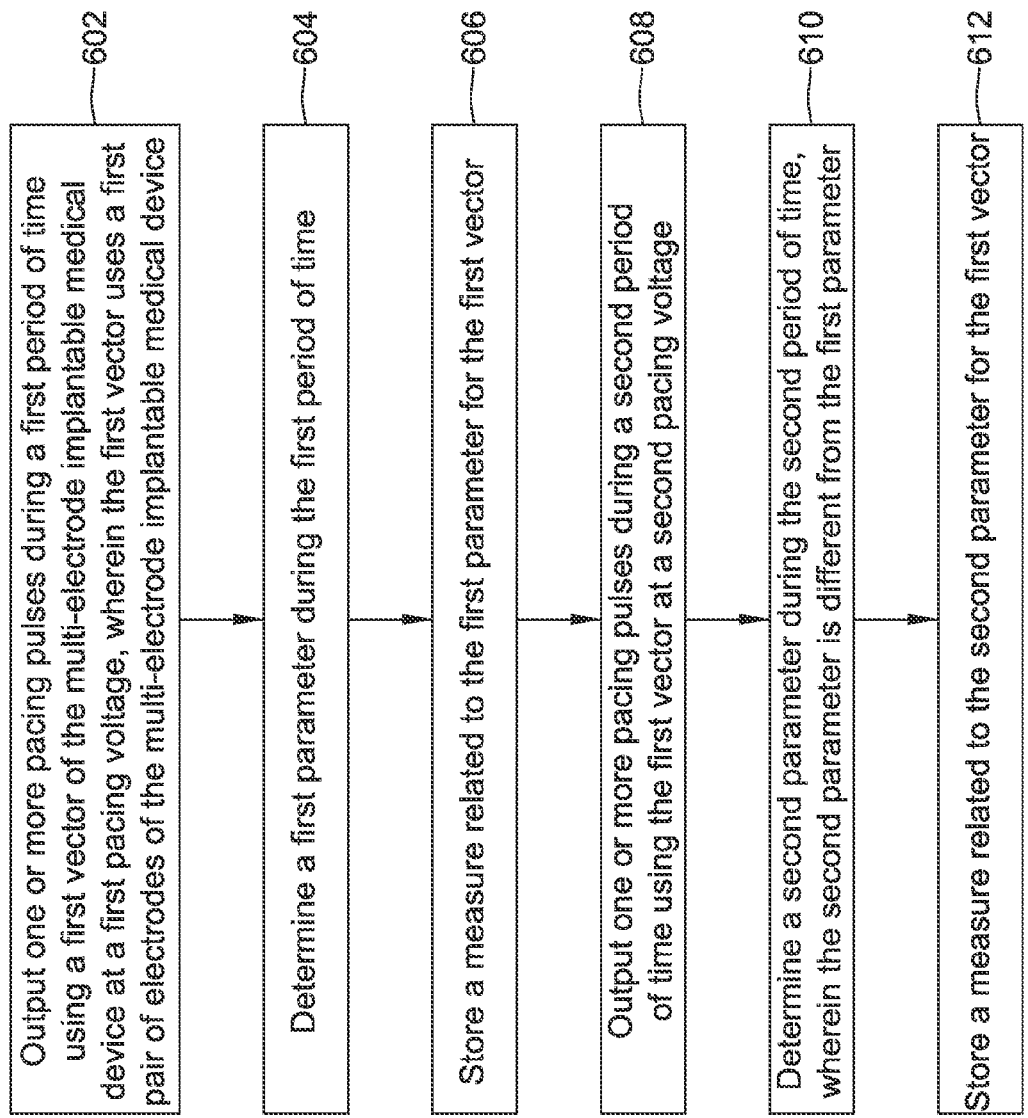
FIG. 6 shows a flow diagram of an illustrative method that may be implemented by an implantable medical device system such as the implantable medical system of FIG. 1.

FIG. 6 shows a flow diagram of an illustrative method that may be implemented by an implantable medical device system such as the implantable medical device system of FIG. 1. Although the method of FIG. 6 will be described with respect to the implantable medical device system of FIG. 1, it is contemplated that the method of FIG. 6 may be performed by any suitable medical device system.

A medical device system, such as system 100 of FIG. 1, including implantable medical device 101 and/or external assembly 140, may output one or more pacing pulses during a first period of time using a first vector of the multi-electrode implantable medical device at a first pacing voltage, wherein the first vector uses a first pair of electrodes of the multi-electrode implantable medical device, as shown at 602. In one example, as described above, system 100 may deliver electrical stimulation therapy (e.g. pacing pulses) at voltage amplitude V1 during a first time period T1. System 100 may then determine a first parameter during the first period of time, as shown at 604. In one example, system 100 may determine an evoked response template or capture detection window for heart 115. In some instances, system 100 may determine an impedance of the current vector. For instance, system 100 may determine a voltage or current and determine an impedance value using Ohm's Law. In still other examples, system 100 may determine a signal related to phrenic nerve stimulation. In some examples, system 100 may determine one or more parameters different from a presence of phrenic nerve stimulation, impedance, and an evoked response template, as desired.

System 100 may store a measure related to the first parameter for the first vector, as shown at 606. For example, system 100 may store a determination of the impedance, presence of phrenic nerve stimulation, and/or evoked response template in a memory, such as memory circuit 104 or memory circuit 144. System 100 may store a particular Ohm value related to the impedance of the first vector. In some examples, system 100 may store a determination of whether system 100 determined a presence of phrenic nerve stimulation. In other examples, system 100 may store a determination of whether system 100 determined a presence of phrenic nerve stimulation, and if system 100 determined a presence of phrenic nerve stimulation, system 100 may additionally store a voltage value.

System 100 may output one or more pacing pulses during a second period of time using the first vector at a second pacing voltage, as shown at 608. For example, system 100 may deliver electrical stimulation therapy during a second time period T2 and at a second voltage amplitude V2. System 100 may then determine a second parameter during the second period of time, wherein the second parameter is different from the first parameter, as shown at 610. For example, system 100 may determine a capture threshold, in accordance with the techniques described above or other techniques. In other examples, system 100 may determine one of a presence of phrenic nerve stimulation, impedance, or an evoked response template. In still other examples, system 100 may determine other parameters during the second period of time T2. System 100 may store a measure related to the second parameter for the first vector (612). For example, system 100 may store whether system 100 detected a contraction of heart 115 in response to the delivered electrical stimulation. In other examples, system 100 may store a voltage value indicating an approximate minimum voltage required to cause heart 115 to contract in response to delivered electrical stimulation.

Figure 7A:
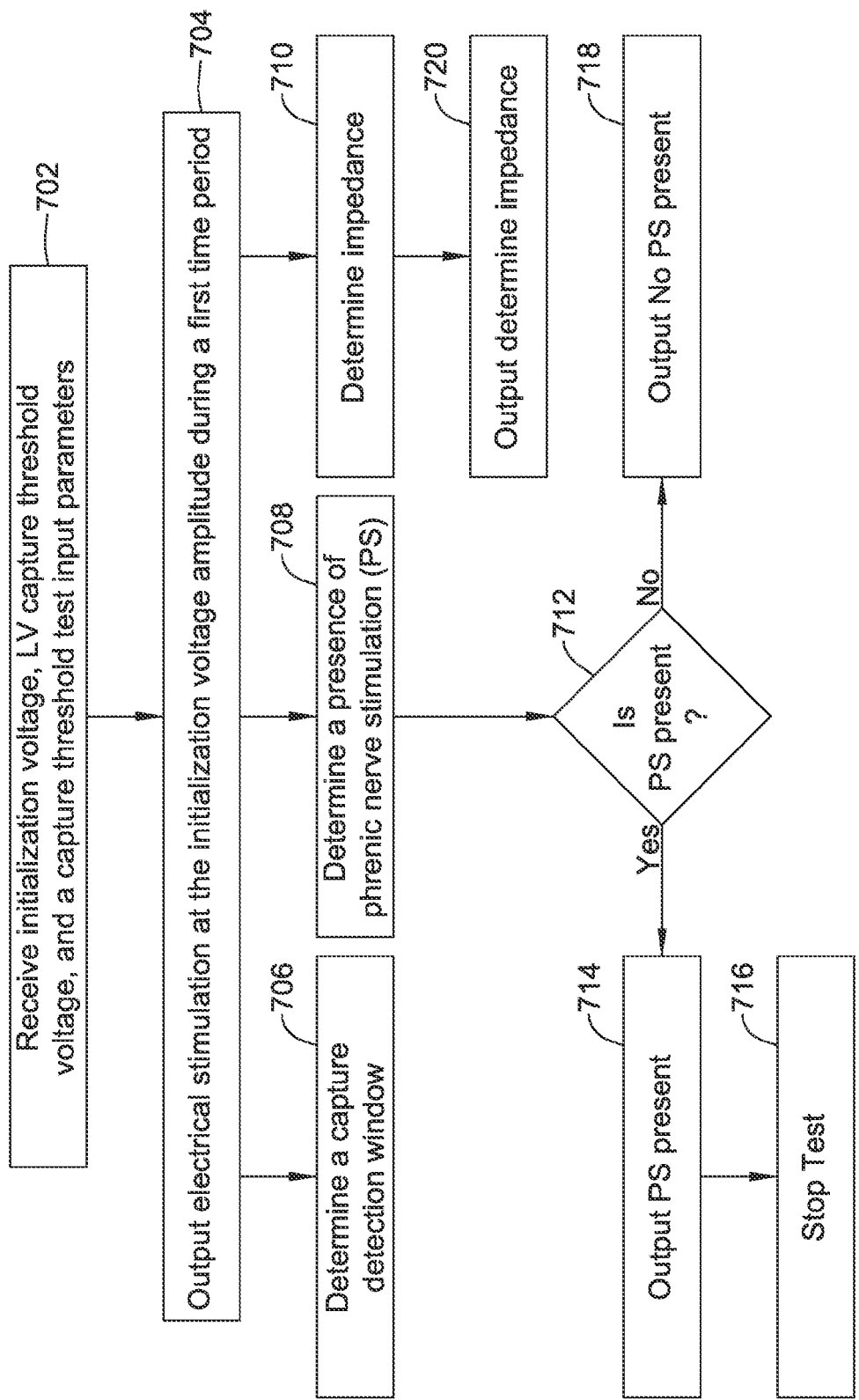
FIGS. 7A-7B show a flow diagram of an illustrative method that may be implemented by an implantable medical device system such as the implantable medical system of FIG. 1.
Figure 7B:
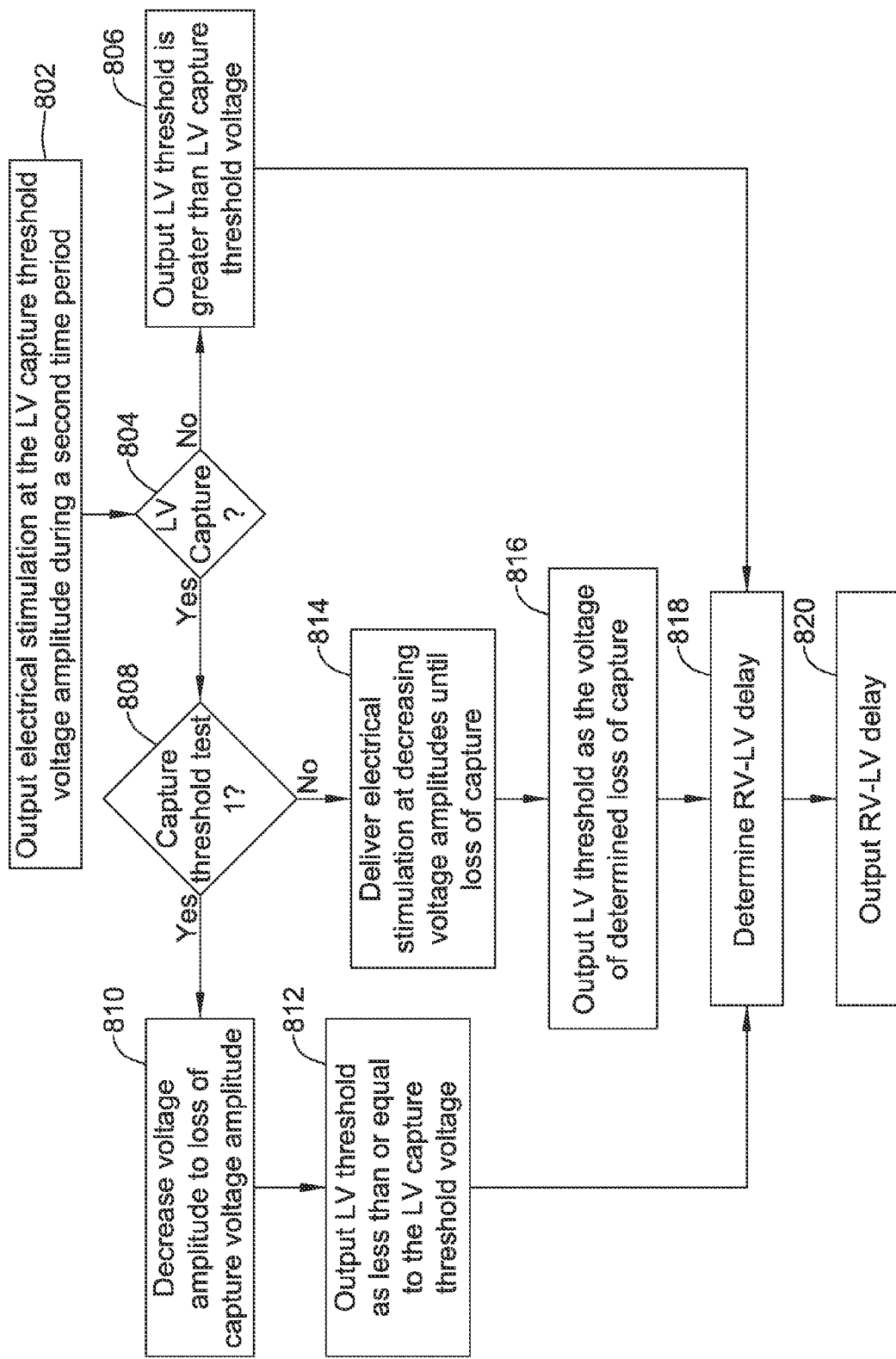

FIGS. 7A-7B show a flow diagram of an illustrative method that may be implemented by an implantable medical device system such as the implantable medical device system of FIG. 1. Although the method of FIGS. 7A-7B will be described with respect to the implantable medical device system of FIG. 1, the method of FIGS. 7A-7B may be performed by any suitable medical device system.

A medical device system, such as system 100 of FIG. 1, including implantable medical device 101 and/or external assembly 140, may receive an initialization voltage, LV capture threshold voltage, and capture threshold test input parameters, as shown at 702. In some instances, system 100 may allow for a user to input information into system 100 which may affect the vector assessment. Some example inputs include an initialization voltage (e.g. V1), an LV capture threshold voltage (e.g. V2), and a capture threshold test type (step-up, step-down, binary, etc.). Additional example parameters may include a length of time of time period T1, such as in seconds, number of delivered pacing pulses, or heart beats. An initialization voltage (e.g. V1) may be a voltage amplitude at which system 100 begins delivering electrical stimulation during a vector assessment. In some example, system 100 may use the input initialization voltage as voltage amplitude V1. An LV capture threshold voltage may be a voltage amplitude that system 100 may use for determining a capture threshold. For example, system 100 may use an input LV capture threshold voltage as voltage amplitude V2 when determining a capture threshold during a vector assessment. In some examples, LV threshold capture voltage may represent a voltage amplitude that is deemed to be an acceptable electrical stimulation voltage for subsequent pacing (e.g. 2.5 V), so long as it captures the heart.

The capture threshold test input parameter may indicate which capture threshold that system 100 will use when performing a capture threshold test. For example, a user may enter an indication of a first capture threshold test type or a second capture threshold test type. If a user selects a first capture threshold test type, system 100 may perform a capture threshold test in accordance with the techniques described above for the step-wise capture threshold test. If a user selects a second capture threshold test type, system 100 may perform a capture threshold test in accordance with the techniques described above for the binary-threshold capture test.

In some examples, instead of receiving input parameters, such parameters are predetermined. For example, system 100 may store in memory an initialization voltage, an LV capture threshold voltage, and a capture threshold test input parameter. Accordingly, instead of receiving such parameters as input from a user, system 100 may simply read such parameters from memory. Of course, in other examples, system 100 may store some of the parameters and receive as input other of the parameters. In still other examples, system 100 may store all of the parameters, but still allow a user to override the stored parameters with input parameters. In yet other examples, such parameters may be hard coded into system 100.

After receiving the input parameters (if applicable), system 100 may output electrical stimulation at the initialization voltage amplitude during a first time period, as shown at 704. For example, system 100 may deliver pacing pulses or other electrical stimulation therapy at the initialization voltage amplitude. In some examples, the first time period includes of a length of twelve beats, or twelve delivered pacing pulses. In other examples, a user may enter an input parameter indicating a length of time for the first time period. In such examples, system 100 may use the input time period as the length of time for the first time period.

During the delivery of electrical stimulation during the first time period, system 100 may determine an evoked response template or capture detection window for heart 115, sometimes based on the amplitude of each of a series of evoked response signals, as shown at 706. Such a capture detection window may be used to identify when system 100 actively senses for an evoked response during a subsequent capture detection test.

System 100 may, during the delivery of electrical stimulation during the first time period, determine a presence of phrenic nerve stimulation (PS), as shown at 708. For example, system 100 may receive an input signal from a sensor, such as an accelerometer. System 100 may then determine, based on the signal level and/or signal morphology of the accelerometer signal whether a delivered pacing pulse has caused stimulation of the phrenic nerve. In other examples, system 100 may determine, based on the morphology of an evoked response signal, whether a delivered pacing pulse has caused stimulation of the phrenic nerve. In some cases, a physician may input for each pacing pulse whether phrenic stimulation was observed.

If system 100 determines that a delivered pacing pulse has caused PS (yes branch at 712), system 100 may output PS Present as shown at 714. For example, system 100 may output, such as to user interface 145, that system 100 detected a presence of PS. In some examples, system 100 may fill one or more cells of a table output to user interface 145 with the phrenic nerve stimulation determination, such as table 400 of FIG. 5. Also, and in some examples, system 100 may stop the vector assessment for that vector when phrenic stimulation is detected, as shown at 716. If system 100 determines that a delivered pacing pulse has not caused PS (no branch of 712), system 100 may output No PS Present, as shown at 718. For example, system 100 may output, such as to user interface 145, that system 100 detected no presence of PS. In some examples, system 100 may fill one or more cells of a table output to user interface 145, such as table 400 of FIG. 5.

In some instances, system 100 may also determine an impedance of the vector, as shown at 710. For example, system 100 may deliver a voltage or current pulse via the vector and measure a current through the vector or a resulting voltage across the electro-stimulation electrodes of the vector. Subsequently, using Ohm's Law, system 100 may determine an impedance for the vector. In some examples, system 100 may use one or more of the delivered pacing pulses as the delivered voltage or current pulse in order to determine the impedance for the vector.

Once system 100 has determined an evoked response template and/or capture detection window, determined a presence of phrenic nerve stimulation, and determined and impedance for the vector, and/or that system 100 has reached the end of the first time period, system 100 may reduce the voltage amplitude of the delivered electrical stimulation and perform a capture threshold test and in some cases other actions, as described below with respect to FIG. 7B.

A medical device system, such as system 100 of FIG. 1, including implantable medical device 101 and/or external assembly 140, may deliver electrical stimulation at the LV capture threshold voltage amplitude during a second time period, as shown at 802. After delivering the electrical stimulation at the LV capture threshold voltage amplitude, system 100 may determine whether the electrical stimulation captured heart 115, as shown at 804. For example, system 100 may actively sense for an evoked response during a capture detection window determined previously.

If system 100 determines that the delivered electrical stimulation did not capture heart 115 (no branch of 804), system 100 may output a determination that the capture threshold of the vector is greater than the LV capture threshold voltage, as shown at 806. In some examples, system 100 may fill one or more cells of a table that is output to user interface 145 with the determined capture threshold information, for example table 400 of FIG. 5.

If system 100 determines that the delivered electrical stimulation did capture heart 115 (yes branch of 804), system 100 may determine whether a user selected a first capture threshold test type, as shown at 808. If a user did select the first capture threshold test type (yes branch of 808), system 100 may decrease the voltage amplitude of the delivered electrical stimulation to a loss of capture voltage amplitude, as shown at 810. For example, system 100 may decrease the voltage amplitude of the delivered electrical stimulation to 0V, 0.1V, 0.2V, or any other suitable loss of capture voltage. In some instances, the first capture threshold test type may correspond to the binary-threshold capture technique disclosed herein. In some examples, system 100 may additionally determine that electrical stimulation delivered at the loss of capture voltage amplitude does not result in capture of heart 115. System 100 may then output a capture threshold as less than or equal to the LV capture threshold voltage (812). For example, system 100 may fill one or more cells of a table output to user interface 145 with the capture threshold information, for example table 400 of FIG. 5.

If a user selected a second capture threshold test (no branch of 808), system 100 may deliver electrical stimulation at decreasing voltage amplitudes until system 100 determines that delivered electrical stimulation has failed to capture heart 115, as shown at 814. In this example, the second capture threshold test type corresponds to the step-down capture threshold technique disclosed herein. In some instances, system 100 may deliver electrical stimulation at a first voltage amplitude less than the LV capture threshold voltage and determine whether the delivered electrical stimulation captures the heart 115. Upon determining that the stimulation does capture heart 115, system 100 may deliver electrical stimulation at a second voltage amplitude less than the first voltage amplitude and again determine whether the delivered electrical stimulation captures heart 115. System 100 may repeat this process until system 100 determines that the delivered electrical stimulation does not capture heart 115. Once system 100 determines that delivered electrical stimulation does not capture heart 115, system 100 may output a capture threshold, as shown at 816. In some cases, system 100 may output the capture threshold as the lowest voltage level of delivered electrical stimulation where system 100 determined that the electrical stimulation captured the heart 115.

Once system 100 has determined that delivered electrical stimulation has failed to capture heart 115, either at 810, 814, or 806, system 100 may in some cases determine an RV-LV delay for the vector, as shown at 818. For example, system 100 may deliver electrical stimulation to a first electro-stimulation electrode of the current vector and determine an elapsed time before detecting the delivered electrical stimulation at the second electro-stimulation electrode of the current vector. In other examples, system 100 may measure a difference in time when system 100 detects a QRS wave of an intrinsic depolarization of heart 115 at a first electro-stimulation electrode and when system 100 detects that same depolarization wave at a second electro-stimulation electrode. From this, system 100 may determine an RV-LV delay of the vector. In some examples, system 100 may continue to determine an RV-LV delay for a vector with each intrinsic depolarization of heart 115. Once system 100 has determined that the RV-LV delay has stabilized, for example by determining a difference between consecutive determined RV-LV delays of no more than 10 ms, 7.5 ms, 5 ms, 3 ms, 2 ms, or any other suitable time, system 100 may determine the stabilized RV-LV delay as the RV-LV delay of the vector. In other examples, system 100 may determine that the RV-LV delay has stabilized when the RV-LV delays between consecutive RV-LV delays is no more than 10%, 7.5%, 5%, 2.5%, or any other suitable percent difference. In still other examples, system 100 may use more than just two consecutive determined RV-LV delays to determine stability of the RV-LV delay of the vector (e.g. a trend based on three or more RV-LV delays)

Once system 100 has determined an RV-LV delay for the current vector, system 100 may output the determined RV-LV delay, as shown at 820. For example, system 100 may fill one or more cells of a table output to user interface 145 with the determined RV-LV delay, for example table 400 of FIG. 5.

Those skilled in the art will recognize that the present disclosure may be manifested in a variety of forms other than the specific embodiments described and contemplated herein. Accordingly, departure in form and detail may be made without departing from the scope and spirit of the present disclosure as described in the appended claims.

What is claimed is:

1. A method of determining parameters for each of a plurality of vectors of a multi-electrode implantable medical device, the method comprising, in a single sequence having first, second, and third time periods:
   in the first time period:
      outputting one or more pacing pulses using a first vector of the multi-electrode implantable medical device at an initialization voltage, the first vector defined by a first pair of electrodes of the multi-electrode implantable medical device;
      determining a presence of phrenic stimulation and an impedance between the first pair of electrodes in response to the one or more pacing pulses output at the initialization voltage;
      storing a measure related to the presence of phrenic stimulation and a measure related to the determined impedance between the first pair of electrodes for the first vector at the initialization voltage;
   in the second time period:
      stepping down the initialization voltage to a second pacing voltage;
      outputting one or more pacing pulses using the first vector at the second pacing voltage;
      determining whether capture occurs in response to the one or more pacing pulses output at the second pacing voltage;
      storing a measure related to whether capture occurs for the first vector at the second pacing voltage; and
   in the third time period:
      stepping down the second pacing voltage to a third pacing voltage;
      outputting one or more pacing pulses using the first vector at the third pacing voltage;
      determining an electrical delay for the first vector in response to the one or more pacing pulses output at the third pacing voltage; and
      storing a measure related to the determined electrical delay for the first vector at the third pacing voltage.

2. The method of claim 1, further comprising:
   providing a set of parameters for the first vector to an external assembly, and
   wherein the set of parameters for the first vector include measures stored during the single sequence.

3. The method of claim 1, further comprising, in the third time period:

determining a stability of the determined electrical delay during the third time period at the third pacing voltage;

storing a measure related to the stability of the determined electrical delay timing for the first vector.

4. The method of claim 1, further comprising, in the second time period:

stepping down the second pacing voltage until capture is not detected using the sensing circuit, and storing a measure related to a lowest voltage that capture is detected using the sensing circuit during the second time period.

5. The method of claim 1, wherein the initialization voltage is selectable by a user.

6. The method of claim 1, further comprising, in the first time period:

terminating the single sequence if the presence of phrenic nerve stimulation is positive during the first time period at the initialization voltage.

7. The method of claim 1, wherein the electrical delay includes one or more of an RV-LV delay or a QLV delay.

8. The method of claim 1, further comprising, in the third time period:

determining an R-wave amplitude for the first vector in response to the one or more pacing pulses output at the third pacing voltage; and storing a measure related to the R-wave amplitude for the first vector at the third pacing voltage.

9. A multi-electrode implantable medical device for determining parameters for each of a plurality of vectors in a single sequence having first, second, and third time periods, the device comprising:

a pulse generator;
a sensing circuit; and
a controller circuit,
wherein, in the first time period:

the pulse generator is configured to output one or more pacing pulses using a first vector of the multi-electrode implantable medical device at an initialization voltage, the first vector defined by a first pair of electrodes of the multi-electrode implantable medical device;

the sensing circuit is configured to determine a presence of phrenic stimulation and an impedance between the first pair of electrodes in response to the one or more pacing pulses output at the initialization voltage; and the controller circuit configured to store a measure related to the presence of phrenic stimulation and a measure related to the determined impedance between the first pair of electrodes for the first vector at the initialization voltage, wherein, in the second time period:

the controller is configured to step down the initial voltage to a second pacing voltage;

the pulse generator is configured to output one or more pacing pulses using the first vector at the second pacing voltage;

the sensing circuit is configured to determine whether capture occurs in response to the one or more pacing pulses output at the second pacing voltage; and the controller circuit is configured to store a measure related to whether capture occurs for the first vector at the second pacing voltage, and wherein, in the third time period:

the controller is configured to step down the second pacing voltage to a third pacing voltage;

the pulse generator is configured to output one or more pacing pulses using the first vector at the third pacing voltage;

the sensing circuit is configured to determine an electrical delay for the first vector in response to the one or more pacing pulses output at the third pacing voltage; and the controller is configured to store a measure related to the determined electrical delay for the first vector at the third pacing voltage.

10. The system of claim 9, further comprising:

a communication circuit configured to provide a set of parameters for the first vector to an external assembly, wherein the parameters for the first vector include measures stored during the single sequence.

11. The system of claim 10, wherein, in the third time period:

the sensing circuit is configured to determine a stability of the determined electrical delay during the third time period at the third pacing voltage; and the controller circuit is configured to store a measure related to the stability of the determined electrical delay.

12. The system of claim 9, wherein, in the second time period:

the controller circuit is configured to step down the second pacing voltage until the sensing circuit does not detect capture, and to store a measure related to a lowest voltage at which the sensing circuit determines that capture occurs.

13. The system of claim 9, wherein the initialization voltage is selectable by a user.

14. The system of claim 9, wherein, in the first time period:

the controller is configured to terminate the single sequence if the sensing circuit determines that phrenic nerve stimulation occurs at the initialization voltage.

15. The system of claim 9, wherein the electrical delay includes one or more of an RV-LV delay or a QLV delay.

16. The system of claim 9, wherein, in the third time period:

the sensing circuit is configured to determine an R-wave amplitude for the first vector in response to the one or more pacing pulses output at the third pacing voltage; and the controller circuit is configured to store a measure related to the determined R-wave amplitude for the first vector at the third pacing voltage.

17. A non-transitory machine readable medium, the non-transitory machine readable medium containing instructions, which, when executed by a processor, cause the processor to perform operations for determining parameters for each of a plurality of vectors of a multi-electrode implantable medical device in a single sequence having first, second, and third time periods, the operations comprising:

in the first time period:

outputting one or more pacing pulses using a first vector of the multi-electrode implantable medical device at an initialization voltage, the first vector defined by a first pair of electrodes of the multi-electrode implantable medical device;

determining a presence of phrenic stimulation and an impedance between the first pair of electrodes in response to the one or more pacing pulses output at the initialization voltage;

storing a measure related to the presence of phrenic stimulation and a measure related to the impedance between the first pair of electrodes for the first vector at the initialization voltage;

in the second time period:

stepping down the initialization voltage to a second pacing voltage;

outputting one or more pacing pulses using the first vector at the second pacing voltage;

determining whether capture occurs in response to the one or more pacing pulses output at the second pacing voltage;

storing a measure related to whether capture occurs for the first vector at the second pacing voltage; and in the third time period:

stepping down the second pacing voltage to a third pacing voltage;

outputting one or more pacing pulses using the first vector at the third pacing voltage;

determining an electrical delay for the first vector in response to the one or more pacing pulses output at the third pacing voltage; and storing a measure related to the determined electrical delay for the first vector at the third pacing voltage.

18. The machine readable medium of claim 17, the operations further comprising: in the second time period:

stepping down the second pacing voltage until capture is not detected using the sensing circuit; and storing a measure related to a lowest voltage that capture is detected using the sensing circuit during the second time period.

19. The machine readable medium of claim 17, wherein the electrical delay includes one or more of an RV-LV delay or a QLV delay.

20. The machine readable medium of claim 17, the operations further comprising: in the third time period:

determining an R-wave amplitude for the first vector in response to the one or more pacing pulses output at the third pacing voltage; an storing a measure related to the determined R-wave amplitude for the first vector at the third pacing voltage.

* * * * *